US012086975B2

(12) United States Patent
Zhang

(10) Patent No.: US 12,086,975 B2
(45) Date of Patent: Sep. 10, 2024

(54) SYSTEMS, METHODS, AND COMPUTER-READABLE MEDIA FOR EVALUATING MICROSTRUCTURAL EQUIVALENCE

(71) Applicant: DigiM Solution LLC, Winchester, MA (US)

(72) Inventor: Shuang Zhang, Winchester, MA (US)

(73) Assignee: DIGIM SOLUTION LLC, Winchester, MA (US)

( * ) Notice: Subject to any disclaimer, the term of this patent is extended or adjusted under 35 U.S.C. 154(b) by 415 days.

(21) Appl. No.: 17/586,197

(22) Filed: Jan. 27, 2022

(65) Prior Publication Data

US 2022/0237773 A1      Jul. 28, 2022

Related U.S. Application Data

(60) Provisional application No. 63/142,142, filed on Jan. 27, 2021.

(51) Int. Cl.
*G06T 7/00* (2017.01)
*G06T 7/55* (2017.01)
*G16H 20/10* (2018.01)

(52) U.S. Cl.
CPC .......... *G06T 7/0006* (2013.01); *G06T 7/001* (2013.01); *G06T 7/55* (2017.01); *G16H 20/10* (2018.01)

(58) Field of Classification Search
USPC ....................................................... 382/141
See application file for complete search history.

(56) References Cited

U.S. PATENT DOCUMENTS

2013/0208958 A1* 8/2013 Tomoto ..................... G06T 7/49
382/128

OTHER PUBLICATIONS

The Pharmaceutical Development Group: Importance and Excellent Benefits of Generic Drugs. Retrieved from the Internet on Oct. 25, 2022, https://pharmdevgroup.com/importance-and-excellent-benefits-of-generic-drugs/.
Drugs@FDA Glossary of Terms; Retrieved from the Internet on Oct. 25, 2022, https://www.fda.gov/drugs/drug-approvals-and-databases/drugsfda-glossary-terms#RLD.
Yu, Lawrence X., et al., FDA Bioequivalence Standards, AAPS Advances in the Pharmaceutical Sciences Series 13 Eds., Springer 2014. https://doi.org/10.1007/978-1-4939-1252-0.

(Continued)

*Primary Examiner* — Jacky X Zheng
(74) *Attorney, Agent, or Firm* — Hamilton, Brook, Smith & Reynolds, P.C.

(57) ABSTRACT

A method using high resolution imaging data, artificial intelligence-based quantitative image analytics, and image-based release prediction is disclosed to facilitate the determination of microstructure equivalence between two representative samples, such as pharmaceutical and material products. A computer-implemented method of evaluating microstructural equivalence of samples includes quantitatively comparing corresponding parameters of microstructure feature matrices, such as parameters for particle size distribution, porosity, uniformity of spatial distribution, and release rate of a material phase, to permit evaluating whether the samples meet a microstructural equivalence standard within an error tolerance.

20 Claims, 12 Drawing Sheets
(9 of 12 Drawing Sheet(s) Filed in Color)

(56) References Cited

OTHER PUBLICATIONS

Gajjar, P et al., "Unlocking the Microstructure of Inhalation Blends Using X-Ray Microscopy," Respiratory Drug Delivery 2020.

Kryscio, David R., "Spreadability Measurements to Assess Structural Equivalence (Q3) of Topical Formulations—A Technical Note," AAPS PharmSciTech, vol. 9, No. 1, Mar. 2008.

Bioequivalence Studies with Pharmacokinetic Endpoints for Drugs Submitted Under an ANDA Guidance for Industry—Draft Guidance; U.S. Department of Health and Human Services, Food and Drug Administration, Center for Drug Evaluation and Research (CDER), Aug. 2021, https://www.fda.gov/media/91553/download.

Zhao, Longshan, et al., "Bioequivalence and Population Pharmacokinetic Modeling of Two Forms of Antibiotic, Cefuroxime Lysine and Cerfuroxime Sodium, After intravenous Infusion in Beagle Dogs," J Biomed Biotechnol. 2012; 2012;507294.

The University of Cambridge—DoITPoMS, Raman Spectroscopy; Retrieved from the Internet on Oct. 25, 2022; http://web.archive.org/web/20120511102714/http://www.doitpoms.ac.uk/tlplib/raman/intro.php.

Mayo, Sheridan C., et al., I"n-Line Phase-Contrast X-Ray Imaging and Tomography for Materials Science," Materials 2012, 5, 937-965.

Chen, Guang-Hong, et al., "X-Ray Phase Sensitive Imaging Methods: Basic Physical Principles and Potential Medical Applications," Curr Med Imaging Rev., 6(2): 90-99, May 1, 2010.

\* cited by examiner

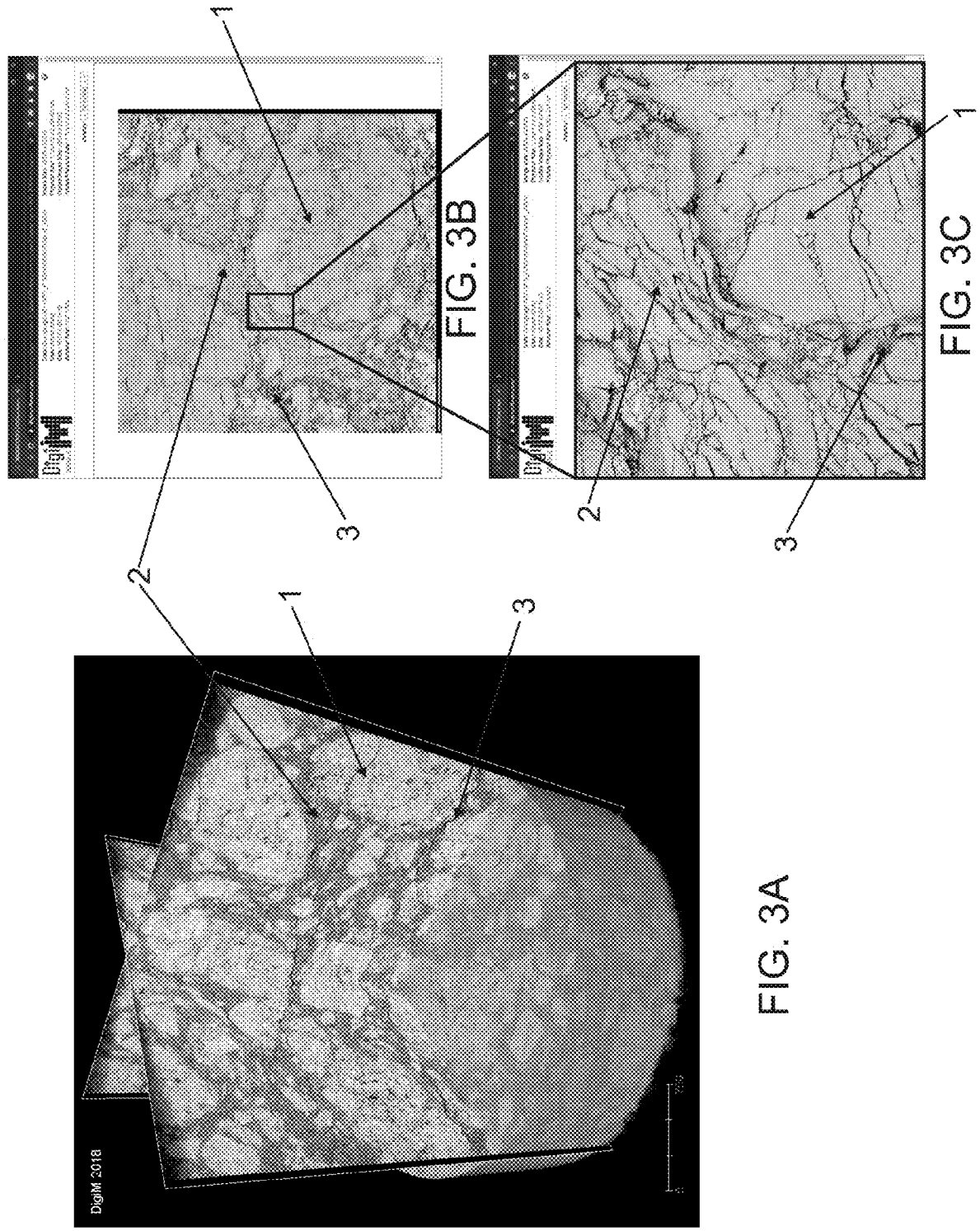

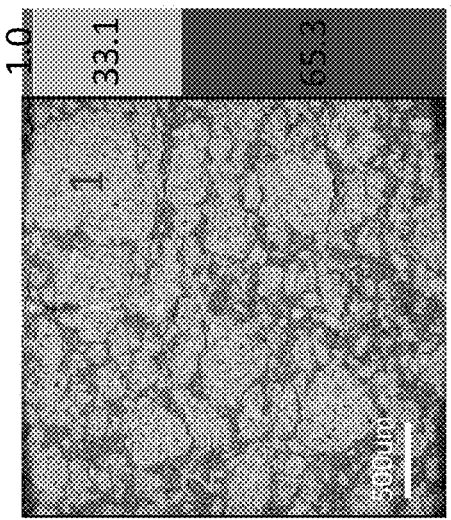
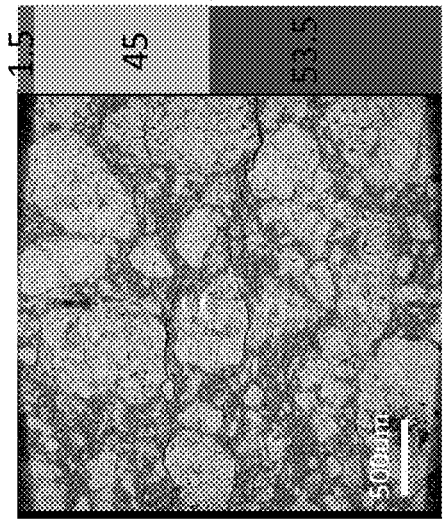
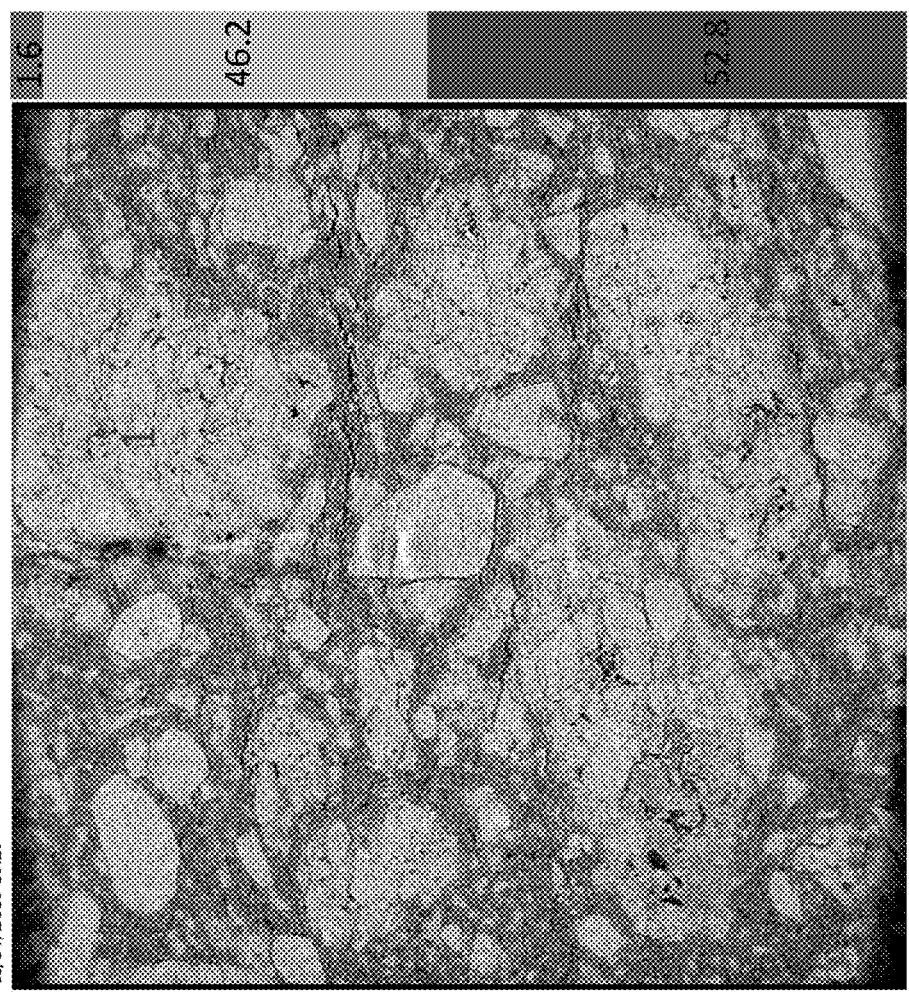
FIG. 6A
FIG. 6B
FIG. 6C

SYSTEMS, METHODS, AND COMPUTER-READABLE MEDIA FOR EVALUATING MICROSTRUCTURAL EQUIVALENCE

RELATED APPLICATION

This application claims the benefit of U.S. Provisional Application No. 63/142,142, filed on Jan. 27, 2021. The entire teachings of the above application are incorporated herein by reference.

BACKGROUND

The equivalence of two material samples is a fundamental question. At the forefront of many different applications rooted in such equivalence evaluation is the development of generic drugs in the pharmaceutical industry. Greater than four out of five prescriptions filled in the U.S. are attributed to generics rather than brand named products. The associated cost savings that generic drugs bring to the U.S. health care system alone is greater than one trillion dollars [1]. Determining equivalence of two drug product samples is one of the key areas for achieving cost saving benefits in drug research and development. Bioequivalence (BE) is defined as "the absence of a significant difference in the rate and extent to which the active ingredient or active moiety in pharmaceutical equivalents or pharmaceutical alternatives becomes available at the site of drug action when administered at the same molar dose under similar conditions in an appropriately designed study" [2]. It is essentially a demonstration that two pharmaceutical products are expected to act equivalently in the human body.

The US Food and Drug Administration (FDA), through its dedicated Office of Generic Drugs (OGD), introduced regulatory guidelines for the pharmaceutical industry based on BE that date back to the 1970s [3]. During this time-period, discrepancies were noticed during a voluntary study with a new cardiac arrythmia drug that had large variations in the reported effects. It was later determined that different amounts of active pharmaceutical ingredients (API) had caused adverse effects. Following further investigations, many variables arose that were believed to play into the differences in the rate and extent of API release including formulation differences, manufacturing differences, dissolution variance, varying particle size distribution, and other factors. Regulations that denote BE emerged as a necessity.

Since that time, BE regulation evolved. Conventional methods to demonstrate that two products are expected to act equivalently in the human body have relied on pharmacokinetics (PK), pharmacodynamics (PD), comparative clinical trials, and in vitro studies. Contextually effective, all these methods are quite time consuming and costly. Furthermore, for products that act locally, i.e., at or near the site of application rather than via the systemic circulation, or act over a long period of time, i.e., for treating chronical disease with improved patient adherence, difficult and expensive clinical endpoint bioequivalence studies that test for clinical cure or improvement with hundreds or thousands of patients are the norm [4]. An enhanced understanding of a drug product and its most likely release behavior emerges as both a regulatory and an economic priority for the FDA.

In response to the drug development trends in the industry, one of the more recent BE regulation revisions incorporates a classification system based on the "degree" of equivalence; Q1, Q2, & Q3 represent the level of those similarities as qualitative (Q1), same compound, quantitative (Q2) same component in the same concentration ($\pm 5\%$ in weight), and microstructural (Q3), same component in the same concentration in the same microstructural arrangement of matter. Microstructures are hence considered as a critical element in BE evaluation, starting with topical and transdermal products such as creams, gels, patches, microneedles, and suspensions [5], and rapidly expanding to long-acting implants, microsphere depots, and intrauterine systems. Therefore, finding suitable tools to determine the microstructural characteristics of drug products has been a priority to both the regulatory agencies and the industry. Furthermore, when pharmaceutical companies consider minor changes in drug formulations, substance sources, process and manufacturing modifications, and/or product repurposing, effective approaches to verifying microstructural characteristics for Q3 BE would be highly desirable for both the industry and regulatory agencies to approve such changes with time and cost efficiency.

Non-Imaging Methods

Conventional BE studies rely heavily on PK, PD, in vitro, in vivo, and clinical endpoint studies [6]. While these are lengthy and costly methods, they are also reasonably reliable and well-established for systemic dosage applications [7]. In contrast, locally acting drugs, do not adhere to the same consistency due to the many interactions related to localized regions. An example of a locally acting drug is one that is topically applied. Once applied, that drug will interact with both the human body and the exterior environment (such as temperature), each of which may affect its therapeutic performance. Finding the right way to characterize such interactions becomes increasingly complicated, which has left a wide range of techniques in question for evaluative purposes.

One of the more frequently cited resources for Q3 BE characterization is Morphologically Directed Ramon Spectroscopy (MDRS) [4]. Raman spectra for a given compound are highly reproducible in different matrices and across different instruments, enabling identification of particles based on spectral matches from a standard spectra library. Raman spectra have multiple extremely sharp lines, providing high spectral resolution, and chemical selectivity. Raman spectra are sensitive enough to distinguish different crystalline polymorphs. It can characterize samples across relatively large dimensions, e.g. a 2D area of a few centimeters by a few centimeters. While this is a highly referenced procedure in Q3 BE literature, its limitations include the weak signal, potential harm to fragile samples, and possible unintended fluorescence of certain structures [8].

Laser Diffraction Analyzers (LDA) are also a popular characterization tool for particle size distribution. Although these are fast and inexpensive (particularly laser light scattering for particle sizing), they do suffer from some serious drawbacks. Unmet needs include:

1) It is difficult, and sometime impossible, to analyze particles embedded/suspended in a solid or semi-solid matrix that is difficult or impossible to access directly.

2) It is imprecise to measure particles with high aspect ratio, particularly when the orientation of the particles in the product is critical to performance.

3) It cannot take account into the channels, voids, cracks, and (micro-)porosity in the sample.

4) It is difficult to analyze products with higher degree of particle/material heterogeneity.

5) Although it has a large dynamic range between 10 nm-3,500 µm, it cannot differentiate particle aggregates from large particles.

6) It cannot be applied to samples that are difficult to manipulate physically (e.g., lyophilized solid, semi-solid, and thermally sensitive gel).

The most pronounced problem with non-imaging methods is the difficulty in assessing particle size in a final drug product. In the case of MDRS, mechanical cutting is often necessary, which can damage the sample and the microstructures therein. LDA can only be used for raw particle ingredients.

Imaging Methods

Microscopic imaging techniques, such as Raman microscopy, near-infrared microscopy, conventional scanning electron microscopy (SEM), and laser light scattering, have been used in drug product characterization, including microstructure bioequivalence studies.

Advancing from earlier MDRS methods, morphologically-directed Raman microscopy (e.g., Morphologi, sold by Malvern Panalytical Ltd. of Malvern, Worcestershire, United Kingdom) provides a technique of automating MDRS spectrum mapping to produce a 2D image. Correlative imaging is supported via survey scans followed by subsequent high-resolution scans of particular particles. With Raman microscopy, however, samples are probed only to a very shallow depth (perhaps from one to a few μm), hence it is not a three-dimensional (3D) characterization method. Raman spectroscopy measures an inherently very weak signal. In order to boost signal to noise ratio, fairly high laser power is needed, which can overheat or even burn samples. Severe fluorescence from some pharmaceutical ingredients precludes analysis of some matrices altogether. Spatial Resolution is limited by optical wavelengths to about 1-2 μm. High-resolution scans, particularly at low laser power and covering large surface areas can have very long acquisition times, and thus be costly.

Near-infrared (NIR) microscopy can be considered to be a poor cousin of Raman microscopy, that is generally less capable, and so is less frequently used in the pharmaceutical industry. NIR spectra have much poorer spectral resolution than Raman, thus more spectral overlap, resulting in worse spatial resolution than Raman. Furthermore, NIR spectra are more influenced by sample conditions, making them less reproducible across different matrices and instruments. This in turn makes it harder to identify particles based on standard spectral libraries and necessitates development of custom spectral libraries. Like Raman microscopy, NIR can be sensitive towards crystalline polymorphism, but less so than Raman. NIR is not limited by sample fluorescence. Because NIR light absorption involves weak overtones of vibrational resonances, NIR light is poorly absorbed by most materials and has tremendous ability to penetrate samples. For example, it is possible to record a usable IR spectrum through a 2"×4" piece of wood. It is also possible to measure the degree of oxygenation of hemoglobin inside the brain by shining NIR light through the skull and measuring the light reflected back through the skull. This extraordinary penetration ability, however, makes it hard to limit the interrogation to just the illuminated spot, due to highly convoluted signal from the neighboring material.

Conventional SEM provides very high spatial resolution. However, it is limited to 2D. Cross-section SEM often requires mechanical preparation of the cross-section surface (e.g., microtom), which often show artifacts (e.g., striations, stray dust particles).

The past decade has led to advancements in x-ray instrument technology that has brought higher resolutions non-invasively. The new capabilities provided with x-ray optical elements have led to the development of x-ray microscopy (XRM). XRM has recently been used as a multiscale characterization tool for inhalation powders, providing information on meso-, micro- and nano-scales [4-8]. Two ways that samples respond by the x-rays passing through them are attenuation and diffraction [9]. First, the x-rays are attenuated, with the absorption proportional to atomic number (Z). Denser elements attenuate x-rays to a greater degree; therefore, materials with varying densities can be categorized through different grayscale values within a reconstructed slice of a 3D dataset. With denser elements, enough contrast exists in the greyscale; however, with low Z (less dense) samples such as organic materials/pharmaceuticals, the greyscale contrast is not sufficient. In the case of low Z materials, the dominant contrast mechanism is through phase shift occurring at particle boundaries or interfaces where there is an appreciable difference in the index of refraction, providing high contrast sensitivity to otherwise weakly absorbing features such as voids, porosity, and boundaries between very similar materials. XRM allows individual drug and excipient particles to be quantified as raw ingredients, intermediate granules, particles, or filaments, and inside the final drug product[4].

Unique to XRM is that it is non-destructive, potentially opening doors as a process analytical technology for production line assessment of formulations within capsules and blisters. There are early signs XRM could potentially unlock the assessment of microstructure of inhaled formulations and provide a bridge between Q3 and BE studies. XRM and quantitative image analytics have demonstrated potential as effective techniques of establishing microstructure bioequivalence, and of evaluating other forms of microstructure equivalence.

SUMMARY

When evaluating equivalence of two drug products, microstructure plays an increasingly important role, particularly, for example, when the release of the active pharmaceutical ingredients is complicated due to controlled release design, locally acting products such as transdermal, topical, or inhaler products, long-acting products such as implants, and complex device-product combinations such as intrauterine systems.

A method using high resolution imaging data, artificial intelligence (AI) based quantitative image analytics, and image-based release prediction is taught herein, to facilitate the determination of microstructure equivalence between two representative samples, such as pharmaceutical and material products. A computer-implemented method of evaluating microstructural equivalence of samples includes quantitatively comparing corresponding parameters of microstructure feature matrices, such as particle size, porosity, uniformity of spatial distribution, and release rate of a material phase, to permit evaluating whether the samples meet a microstructural equivalence standard to a desired degree of error toleration.

One embodiment is a computer-implemented method of evaluating microstructural equivalence of a plurality of samples. The computer-implemented method comprises generating first microstructural image data, stored in a first image data structure, in a manner automated by a computer processor, based on first image data of a microstructure of a first sample; and quantifying the microstructure of the first sample, in a manner automated by the processor, the quantifying comprising generating a first microstructure feature matrix of the first microstructure based on the first microstructural image data, the first microstructure feature matrix stored in a first feature matrix data structure. Microstructural equivalence of the first sample with a second sample is evaluated, in a manner automated by the processor, by quantitatively comparing parameters of the first microstructure feature matrix with corresponding parameters of a second microstructure feature matrix for the second sample, the second microstructure feature matrix stored in a second feature matrix data structure. A quantitative comparison result stored in a comparison result data structure is provided, in a manner automated by the processor, to permit evaluating whether the plurality of samples meet a microstructural equivalence standard within an error tolerance based on results of the quantitatively comparing of the corresponding parameters of the first microstructure feature matrix and the second microstructure feature matrix.

In further, related embodiments, the computer-implemented method may further comprise generating second microstructural image data, stored in a second image data structure, in a manner automated by the processor, based on second image data of a microstructure of the second sample; and quantifying the microstructure of the second sample, in a manner automated by the processor, the quantifying comprising generating the second microstructure feature matrix of the second microstructure based on the second microstructural image data. Evaluating equivalence of the plurality of microstructures may comprise evaluating bioequivalence of a plurality of pharmaceutical products, in a manner automated by the processor, to evaluate whether the plurality of pharmaceutical products comprise a same component, in a same concentration, in a same microstructural arrangement of matter, within an error tolerance. The first sample may comprise a first drug product, and the second sample may comprise a sample of a reference drug product, and evaluating equivalence of the plurality of microstructures may comprise, in a manner automated by the processor, evaluating bioequivalence of the first drug product with the reference drug product. The first drug product may comprise a generic drug product, and the method may comprise performing more than one iteration of: (i) performing correlative imaging of the first drug product and the reference drug product to produce three-dimensional imaging data of the first drug product and the reference drug product; (ii) performing image segmentation of the three-dimensional imaging data of the first drug product and the reference drug product to product segmented three-dimensional imaging data; (iii) statistically analyzing the segmented three-dimensional imaging data to produce critical performance attributes of the first drug product and the reference drug product; (iv) performing image-based release simulations to obtain at least one additional critical performance attribute of the first drug product and the reference drug product; (v) quantitatively comparing the critical performance attributes of the first drug product and the reference drug product to evaluate the bioequivalence of the first drug product with the reference drug product; (vi) if bioequivalence is not found in the comparing of the critical performance attributes, generating optimization feedback for a further iteration of image-based bioequivalence evaluation. Each of the first drug product and the reference drug product may comprise a drug product from the group consisting of: a long-acting polymeric microsphere, an implant, a device, a complex drug, and a combination drug. The first microstructure feature matrix, stored in the first feature matrix data structure, and the second microstructure feature matrix, stored in the second feature matrix data structure, may comprise corresponding matrix parameters for at least one of: particle size distribution of a material phase, porosity of the material phase, uniformity of spatial distribution of the material phase, dissolution rate of the material phase, and release rate of the material phase. Generating the first microstructure feature matrix, stored in the first feature matrix data structure, may comprise using a feature classifier module in a manner automated by the processor to produce the corresponding matrix parameters of the first microstructure feature matrix. Generating the second microstructure feature matrix, stored in the second feature matrix data structure, may comprise using a feature classifier module in a manner automated by the processor to produce the corresponding matrix parameters of the second microstructure feature matrix. At least one of the first microstructural image data stored in the first image data structure and the second microstructural image data stored in the second image data structure may comprise phase segmented image data based at least in part on use of an artificial intelligence engine to produce the phase segmented image data. The release rate of the material phase may be computed with an image-based release prediction model in a manner automated by the processor. The first image data, stored in the first image data structure, may comprise at least one of: x-ray microscopy (XRM) imaging data and focused ion beam scanning electron microscopy (FIB-SEM) imaging data with appropriate contrast and calibration mechanisms. The second image data stored in the second image data structure may comprise at least one of: x-ray microscopy (XRM) imaging data and focused ion beam scanning electron microscopy (FIB-SEM) imaging data with appropriate contrast and calibration mechanisms.

Another embodiment is a computer system for evaluating microstructural equivalence of a plurality of samples. The computer system comprises a first microstructure imaging module configured to generate first microstructural image data, stored in a first image data structure, in a manner automated by a processor, based on first image data of a microstructure of a first sample; and a first microstructure quantification module configured to quantify the microstructure of the first sample, in a manner automated by the processor, the quantifying comprising generating a first microstructure feature matrix of the first microstructure based on the first microstructural image data, the first microstructure feature matrix stored in a first feature matrix data structure. A microstructural equivalence evaluation module is configured to evaluate microstructural equivalence of the first sample with a second sample, in a manner automated by the processor, by quantitatively comparing parameters of the first microstructure feature matrix with corresponding parameters of a second microstructure feature matrix for the second sample, the second microstructure feature matrix stored in a second feature matrix data structure. A quantitative equivalence comparison module is configured to provide, in a manner automated by the processor, a quantitative comparison result stored in a comparison result data structure, to permit evaluating whether the plurality of samples meet a microstructural equivalence standard within an error tolerance based on results of the quantitatively comparing of the corresponding parameters of the first microstructure feature matrix and the second microstructure feature matrix.

In further, related computer system embodiments, the computer system may further comprise a second microstructure imaging module configured to generate second microstructural image data, stored in a second image data structure, in a manner automated by the processor, based on second image data of a microstructure of the second sample; and a second microstructure quantification module configured to quantify the microstructure of the second sample, in a manner automated by the processor, the quantifying comprising generating the second microstructure feature matrix of the second microstructure based on the second microstructural image data. The system may be configured to evaluate bioequivalence of a plurality of pharmaceutical products, in a manner automated by the processor, to evaluate whether the plurality of pharmaceutical products comprise a same component, in a same concentration, in a same microstructural arrangement of matter, within an error tolerance. The first sample may comprise a first drug product, and the second sample may comprise a sample of a reference drug product, and the microstructural equivalence evaluation module may be configured to evaluate equivalence of the plurality of microstructures at least by, in a manner automated by the processor, evaluating bioequivalence of the first drug product with the reference drug product. The first microstructure feature matrix, stored in the first feature matrix data structure, and the second microstructure feature matrix, stored in the second feature matrix data structure, may comprise corresponding matrix parameters for at least one of: particle size distribution of a material phase, porosity of the material phase, uniformity of spatial distribution of the material phase, and release rate of the material phase. The computer system may comprise a feature classifier module configured to generate the first microstructure feature matrix, stored in the first feature matrix data structure, in a manner automated by the processor by producing the corresponding matrix parameters of the first microstructure feature matrix. The feature classifier module may be configured to generate the second microstructure feature matrix, stored in the second feature matrix data structure, in a manner automated by the processor by producing the corresponding matrix parameters of the second microstructure feature matrix. At least one of the first microstructural image data stored in the first image data structure and the second microstructural image data stored in the second image data structure may comprise phase segmented image data based at least in part on use of an artificial intelligence engine to produce the phase segmented image data. The system may be configured to compute the release rate of the material phase with an image-based release prediction model in a manner automated by the processor. The first image data, stored in the first image data structure, may comprise at least one of: x-ray microscopy (XRM) imaging data and focused ion beam scanning electron microscopy (FIB-SEM) imaging data. The second image data, stored in the second image data structure, may comprise at least one of: x-ray microscopy (XRM) imaging data and focused ion beam scanning electron microscopy (FIB-SEM) imaging data.

Another embodiment is a non-transitory computer-readable medium configured to store instructions for evaluating microstructural equivalence of a plurality of samples. The instructions, when loaded into working memory and executed by a processor, cause the processor to evaluate microstructural equivalence of the plurality of samples by: generating first microstructural image data, stored in a first image data structure, in a manner automated by a processor, based on first image data of a microstructure of a first sample; and quantifying the microstructure of the first sample, in a manner automated by the processor, the quantifying comprising generating a first microstructure feature matrix of the first microstructure based on the first microstructural image data, the first microstructure feature matrix stored in a first feature matrix data structure. Microstructural equivalence of the first sample with a second sample is evaluated, in a manner automated by the processor, by quantitatively comparing parameters of the first microstructure feature matrix with corresponding parameters of a second microstructure feature matrix for the second sample, the second microstructure feature matrix stored in a second feature matrix data structure. A quantitative comparison result stored in a comparison result data structure is provided, in a manner automated by the processor, to permit evaluating whether the plurality of samples meet a microstructural equivalence standard within an error tolerance based on results of the quantitatively comparing of the corresponding parameters of the first microstructure feature matrix and the second microstructure feature matrix.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 3A-3C are diagrams showing microstructure imaging to reveal different material phases at various scales using different modality, in accordance with an embodiment of the invention. FIG. 3A shows a 3D XRM image at 3 μm resolution, 6 mm volume FOV, visualized with two cross sections and a partial volume; FIG. 3B shows a large field of view SEM image at 0.1 μm resolution, 2 mm area FOV; and FIG. 3C shows an image that zooms in to the red FOV from FIG. 3B.

FIG. 4A shows one cross section of an XRM volume at 3 μm resolution; FIG. 4B shows an AI-based segmentation corresponding to FIG. 4A; FIG. 4C shows a co-visualization of one cross-section, one segmented cross-section, and partial 3D segmented volume; and FIG. 4D shows a full 3D segmented volume.

FIG. 5A is an image of an RLD Fenbid drug sample and FIG. 5B is an image of a generic drug sample.

FIGS. 6A-6C are diagrams showing Q2 bioequivalence in imaging, in accordance with an embodiment of the invention, in each of which one cross-section of the 3D XRM imaging is shown. FIG. 6A is an image of a glucophase RLD sample; FIG. 6B is an image of a generic drug sample A that does not satisfy Q2 BE; and FIG. 6C is an image of a generic drug sample B that may satisfy Q2 BE.

FIG. 7A is a graph of a PSD of a generic drug that may satisfy Q3 BE, and FIG. 7B is a graph of a PSD of a generic drug that does not satisfy Q3 BE.

FIG. 8A is a graph showing a generic drug that has good uniformity, which is comparable to RLD drug; and FIG. 8B is a graph showing a generic drug that has poorer uniformity than a brand drug.

FIG. 9A is a graph for a generic drug that has a predicted dissolution profile comparable to a brand drug, increasing the chance of satisfying Q3 BE. FIG. 9B is a graph for a generic drug that has a predicted dissolution profile substantially faster than a brand drug, which does not satisfy Q3 BE. The time axis uses an arbitrary unit (a.u.) suggesting applicability for any time scale.

DETAILED DESCRIPTION

A description of example embodiments follows.

Systems, methods, and computer-readable media taught herein use imaging analytics to establish microstructure bioequivalence. While the techniques are exemplified using 3D imaging data such as X-Ray microscopy (XRM) and/or focused ion beam scanning electron microscopy (FIB-SEM), they are also applicable to other types of imaging data.

Overview of Technique

Figure 1:
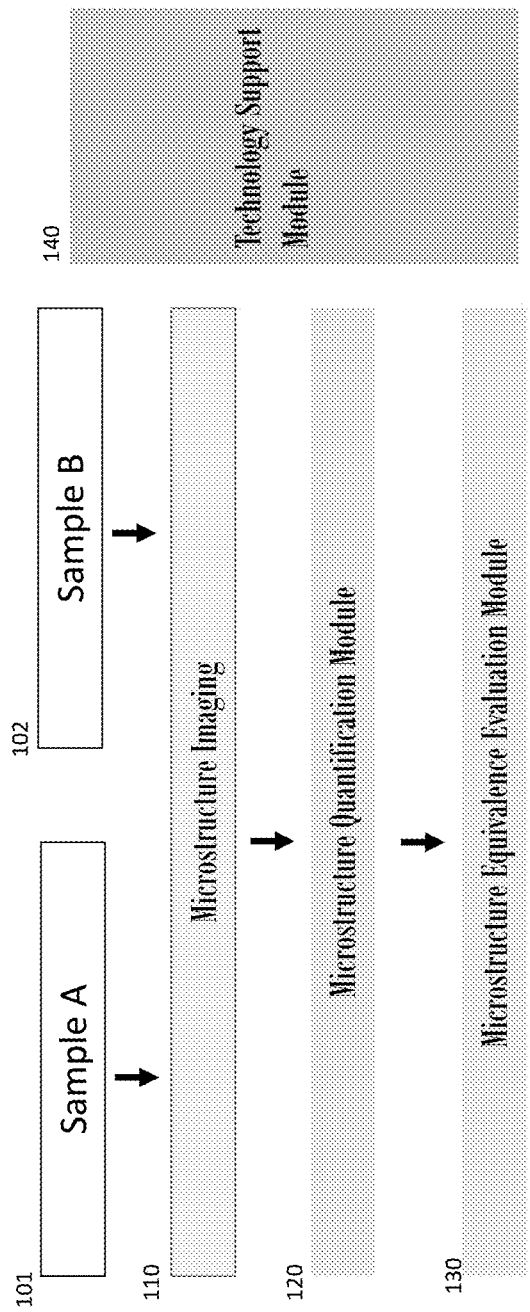
FIG. 1 is a schematic block diagram providing an overview of a system, method, and computer-readable media for determining microstructure equivalence, in accordance with an embodiment of the invention.

FIG. 1 illustrates the overall architecture of the method. In comparison to the conventional, physical laboratory-based microstructure equivalence (used interchangeably with Q3 BE hereafter in the embodiment of this invention, but the learnings can be generalized to the evaluation of the equivalence of any microstructures of any material samples) evaluation approaches, the methodology in this invention is built upon digitization of samples (101 and 102) using a Microstructure Imaging Module (110). Samples A and B each can be a sample from a drug product, a drug API compound, an excipient compound, an intermediate solid, or any material sample. The digitized sample is then analyzed using a Microstructure Quantification Module (120), where a suite of artificial intelligence (AI)-based image analysis tools is employed to quantify critical microstructure features such as particle size distribution of a material phase (such as API), porosity, and uniformity. Physical properties such as dissolution and release can also be predicted. Matrices of sample microstructure parameters are compared using a Microstructure Equivalence Evaluation Module (130).

A suite of enabling tools through a Technology Support Module (140) supports microstructure equivalence evaluation via digital database, compliance and audit tracking, web interface, and necessary high-performance computing hardware, storage, and network facilities.

Applicability of Systems, Methods, and Computer-Readable Media

In generic drug applications, the equivalence of two drug products (used interchangeably with BE hereafter) must generally be assessed when qualifying a new generic to an already-approved originator, or reference listed drug (RLD) product. When such equivalence is established, a biowaiver may be issued by the regulatory agency, which allows generic pharmaceutical companies to bypass the lengthy and costly process required for the approval new drugs.

In addition to generic drug approval, it also frequently comes into play during the development of originator products, for example, when the sponsor conducts its clinical studies with an early prototype formulation, but then seeks to get approval for, and market an improved or repurposed formulation. Equivalence studies are often used to "bridge" the two formulations, rather than going through a new drug application from scratch. In recent years, FDA has made a concerted effort to find in vitro alternatives to clinical endpoint bioequivalence studies in order to help facilitate the development of generic drugs. Many of the products for which such in vitro bioequivalence studies could be done have complicated microstructural features that are often not fully elucidated with currently available technologies. In many cases, approval of the originator product predated modern analytical technology, and so the originator itself may not understand the microstructure of its own product. Systems, methods, and computer-readable media taught herein can, for example, apply to both originator and generic drug development.

After a product is approved, it is common for the sponsor to make changes to the product, e.g., to qualify a new active pharmaceutical ingredient (API) supplier, to make formulation changes, to make manufacturing equipment changes, to make manufacturing process changes, to make manufacturing site changes, etc. Such changes are categorized by FDA as scale up and post-approval changes (SUPAC). FDA has issued guidance that spells out what sort of testing is required to demonstrate that the post-change product is acceptably similar to the pre-change product, but only for two product classes, i.e., solid oral dosage forms and semi-solid dosage forms (creams, ointments, lotions, etc.). Systems, methods, and computer-readable media taught herein can, for example, also apply to the evaluation of the equivalence of pre-change and post-change products, eliminating the need for expensive and time-consuming human studies. This would apply to originator and generic products alike.

The stability of the any of the above-mentioned drug products, over time, transportation, and storage, may also be the subject of a BE study to ensure consistency in performance. This would apply to originator and generic products alike.

Even when all necessary steps are taken, it is inevitable certain BE tests will not pass certain standards. This may be directly linked to the tools used for BE assessment or could be based on a microstructural component that was not captured due to limited resolution of the test provided. Systems, methods, and computer-readable media taught herein can, for example, help to understand the failure of such. In addition, even when traditional methodologies (PK, in vitro, etc.) have been successful for ascertaining Q3 BE, a deeper mechanistic understanding may be desired of the tested product. In such cases, a method for evaluating microstructural details at a high resolution have remained in short supply.

Not only can research and development benefit from the teachings herein, but the manufacturing process itself. The state-of-the-art push for continuous manufacturing would rely heavily on automation and the more simulated functions, the higher efficiency expected. Traditional pharmaceutical manufacturing centers use stepwise systems on large batches, that introduce stops between steps, often due to various locations involved, or in some instances, not having the proper training or staff to move forward. Continuous manufacturing would eliminate the need to stop during a workflow, and enhance the efficiency by a continuous, uninterrupted workflow. Most types of infrastructure changes are best accomplished through gradual changes. Microstructure equivalence from the final drug product offers an eternal gold standard in product quality evaluation. Starting with a verification of the microstructure equivalence (or lack thereof) on formulations out of the lab prior to hitting the continuous workflow, would be a useful implementation of systems, methods, and computer-readable media taught herein.

Other examples of applications of systems, methods, and computer-readable media taught herein include reverse engineering, counterfeit detection, intellectual property protection, litigation, failure analysis, and validation of alternative equivalence methods. Regardless of whether a generic company would expect to demonstrate bioequivalence via pharmacokinetic or clinical endpoint human bioequivalence studies, having a detailed understanding of the microstructure of the target originator product is often highly desirable. Such understanding can help streamline formulation and process development, and potentially improve the likelihood of success of human bioequivalence studies.

Systems, methods, and computer-readable media taught herein can, for example, be applied to products in any of these categories, including but not limited to, oral solid drug, implants, depots, particles or droplets in solid, semi-solid, or liquid suspensions, intrauterine devices, drug eluting devices, combination products, and polymeric products. Furthermore, systems, methods, and computer-readable media taught herein can, for example, be applied to animal medical products, food, and any material samples where one or more material phases (including air) are dispersed into another or more material phases. Hence the terms "product" or "sample" are used in a most general sense, although the embodiments may refer to human drug products.

Detailed Method Workflow and Components

Figure 2:
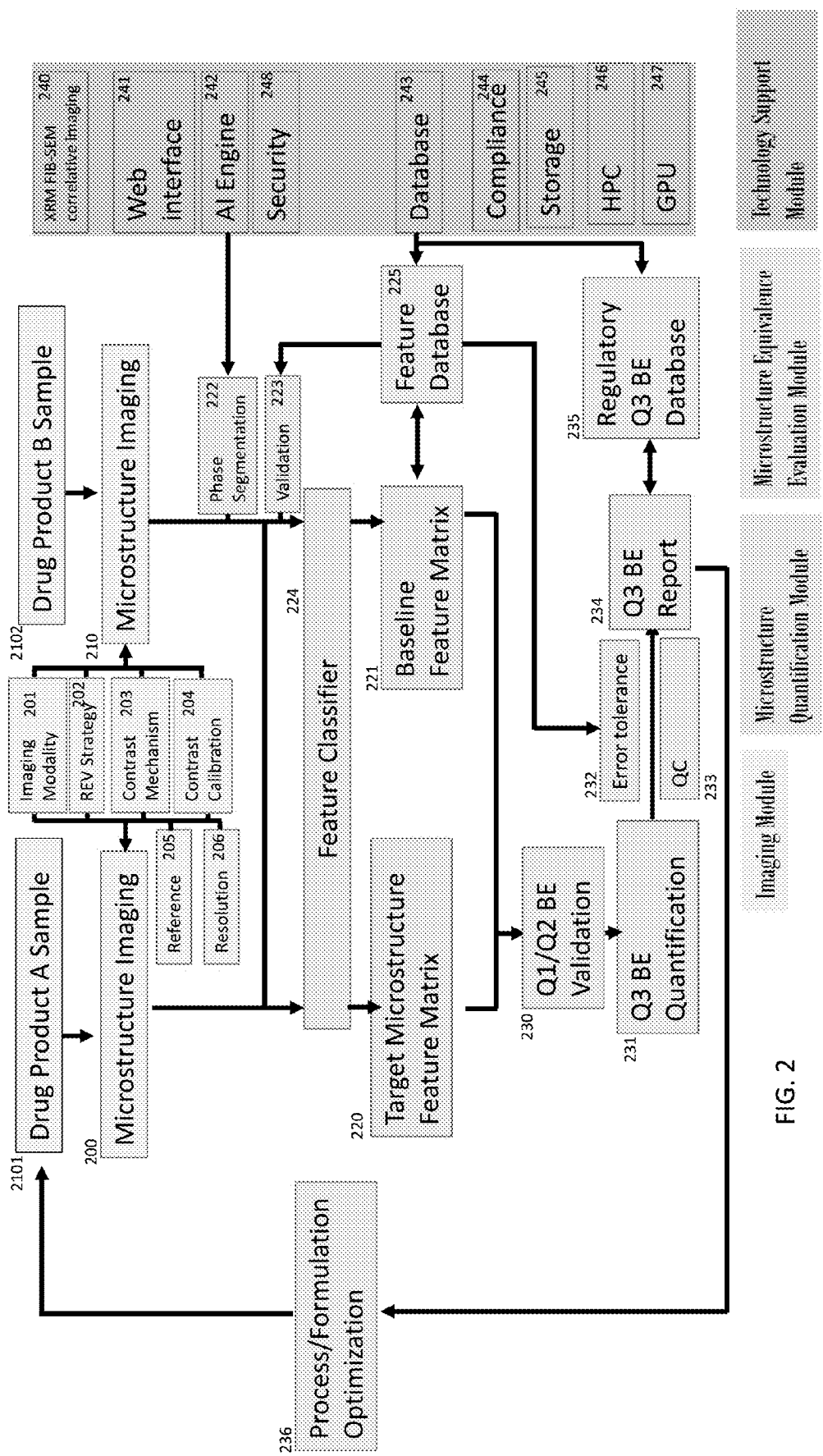
FIG. 2 is a schematic block diagram of a system, method and computer-readable media for determining microstructure (Q3) bioequivalence, based on imaging, in accordance with an embodiment of the invention.

An embodiment of the workflow of the invention in establishing microstructure equivalence of two material samples is illustrated in FIG. 2, with details of the four modules corresponding to the overview illustration of FIG. 1. Drug product A sample 2101 and drug product B sample 2102 of FIG. 2 correspond to samples 101 and 102 of FIG. 1; functional blocks 201-206, 200 and 210 of FIG. 2 are part of an imaging module used to perform microstructure imaging 110 of FIG. 1; functional blocks 220-224 of FIG. 2 are part of a microstructure quantification module 120 of FIG. 1; and functional blocks 225 and 230-236 of FIG. 2 are part of microstructure equivalence evaluation module 130 of FIG. 1. In addition, functional blocks 240-247 of FIG. 2 are part of technology support module 140 of FIG. 1.

The workflow starts with two samples. Sample A (2101) is the sample that is subjected to a microstructure equivalence evaluation. Sample B (2102) is the baseline sample which sample A is evaluated against. In generic drug applications, sample A can be a sample from a new generic product that requires approval, while sample B can be a sample from the RLD product. Sample A can also be a sample from a product similar to a baseline product, but with modified formulation or manufacturing condition, or a material grade change, for example during or after the FDA approval when microstructure equivalence needs to be demonstrated.

Microstructure Imaging

Microstructure imaging of the two drug product samples (200 and 210) is a first step. Six blocks in the imaging module need to be evaluated to ensure successful microstructure imaging, and subsequently the success of digitization of the drug product samples, depending on the product dosage form, sample size, manufacturing method, and size of the API. They are described in the following.

Block 201: Determination of appropriate imaging modality. Appropriate imaging modality is critical to capture the phase contrast, necessary for any successful image-based analytical workflow.

Block 202: Sample representative elementary volume (REV) strategy. This block is to ensure the samples being studied are statistically representative.

Block 203: Contrast mechanism. In some cases, the material phases of interest have large enough molecular structural differences and material density differences to show up in the imaging study with distinctive contrast for each phase. In other cases where the material phase is challenging to establish using as-received samples, contrast enhancement method may be necessary.

Block 204: Contrast calibration. To ensure the quantitative feature matrix is comparable, contrast of the same material phase, e.g., API, need to be calibrated to ensure consistency from the imaging of one sample to the other.

Block 205: Reference standard. In some cases, co-imaging of reference standard made from material with known physical properties (e.g., glass or plastic beads) may be necessary to facilitate contrast calibration.

Block 206: Resolution. Determining the appropriate resolution to resolve critical feature of interest, while keeping a representative enough field of view (FOV), is required. In addition to resolution, other imaging parameters specific to an imaging modality also need to be determined.

The following supporting elements can be used for execution of the microstructure imaging module.

Block 240: Correlative imaging. Correlative imaging is often necessary when the feature of interest demands both high spatial resolution and large FOV.

Block 241 and Block 243: Web interface and Database. The imaging data, potentially conducted at different locations, using different instruments, by different microscopists, need to be archived and logged with a unified protocol, into an easy to access, ideally centralized database, for future analysis, microstructure equivalence evaluation, and compliance auditing.

Block 244: Compliance. The imaging data along with its metadata including all imaging instrument parameters, operation conditions, need to be stored in a reproducible and auditable manner.

Block 245: Storage. Imaging data and metadata need to be stored with good accessibility and security.

FIGS. 3A-3C show one example of a solid drug sample (such as the sample of block 2101 of FIG. 2) after microstructure imaging (as performed in block 200 of FIG. 2), with the following blocks employed. Correlative imaging methodology (block 201 and block 240 of FIG. 2) was used to ensure REV (block 202 of FIG. 2). 3D XRM at 3 µm resolution, 6 mm volume FOV, is illustrated with two cross sections and a partial volume (FIG. 3A; using block 206 of FIG. 2). The contrast of API granule phase (marked as 1 in FIGS. 3A-3C), polymer excipient matrix (marked as 2 in FIGS. 3A-3C), and porosity (marked as 3 in FIGS. 3A-3C) are visualized (using block 203 of FIG. 2). To further reveal the micro-porosity network in the API granule and excipient matrix, a large field of view SEM at 0.1 µm resolution with 2 mm area FOV was used, as shown in FIG. 3B. FIG. 3C shows a zoom-in corresponding to the red FOV from FIG. 3B. Using a correlative imaging approach, a large enough network of granule and polymer matrix is captured via XRM, while the API primary particle and intra-phase microporosity are captured via large FOV SEM.

Microstructure imaging block (210 of FIG. 2), and the subsequent steps (blocks 222, 223, 224 of FIG. 2) can be optional if the baseline feature matrix (block 221 of FIG. 2) has been established previously. In that case, the feature matrix can be pulled out of feature database (block 225 of FIG. 2) without going through block 210 of FIG. 2.

Qualitative and Quantitative Bioequivalence

Microstructure imaging generates a digital representation of the drug samples in terms of grayscale voxel values. Image processing is necessary to convert these grayscale values into parameters that can be used for microstructure equivalence evaluation. Continuing with FIG. 2, a phase segmentation module (222) uses artificial intelligence (AI) engine (242) to build a feature classifier (224). Through validation using independent measurements (223), the feature classifier (224) can be deployed to both Sample A imaging data (200) and Sample B imaging data (210). The former produces a target drug feature matrix (220), while the latter produces a baseline feature matrix (221). The validation data, the feature classifier, and the feature matrix parameters will all be stored in a Feature Database (225) for future reference and reuse. Feature Database (225) is supported by Database block (243), compliance block (244), and storage block (245).

Figure 4A:
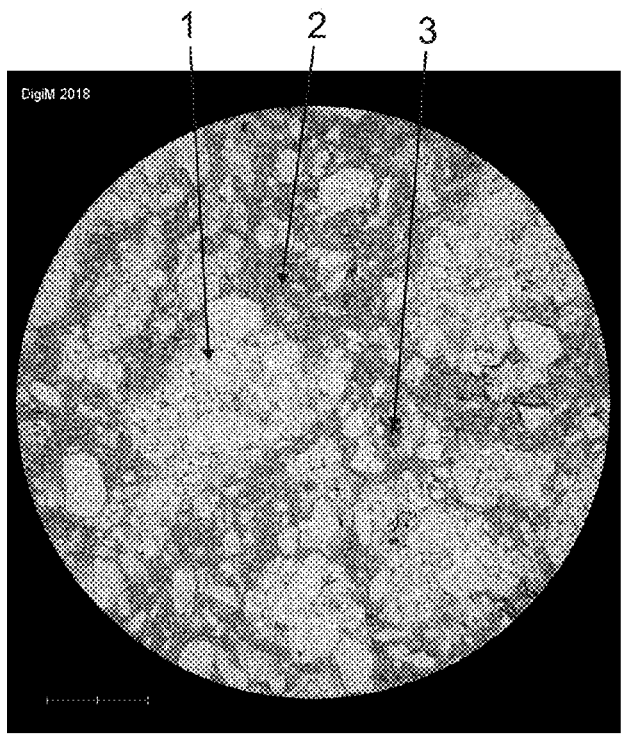
FIGS. 4A-4D are diagrams showing image segmentation in 2D and 3D to reconstruct digital representation of drug microstructures, in accordance with an embodiment of the invention.
Figure 4C:
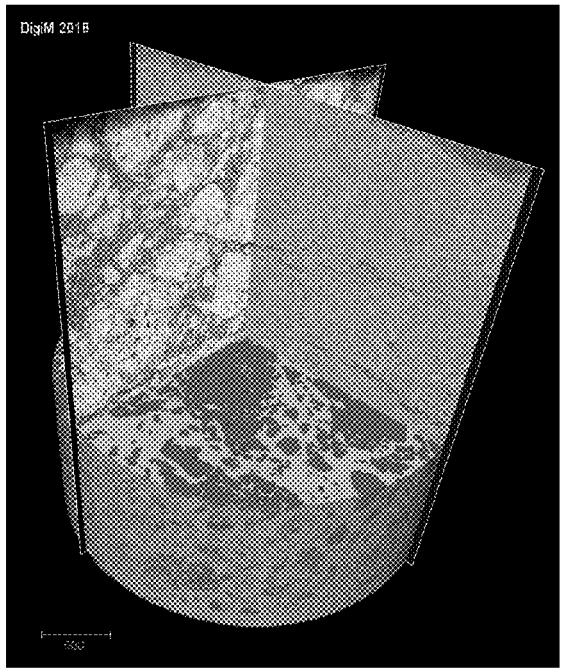
Figure 4B:
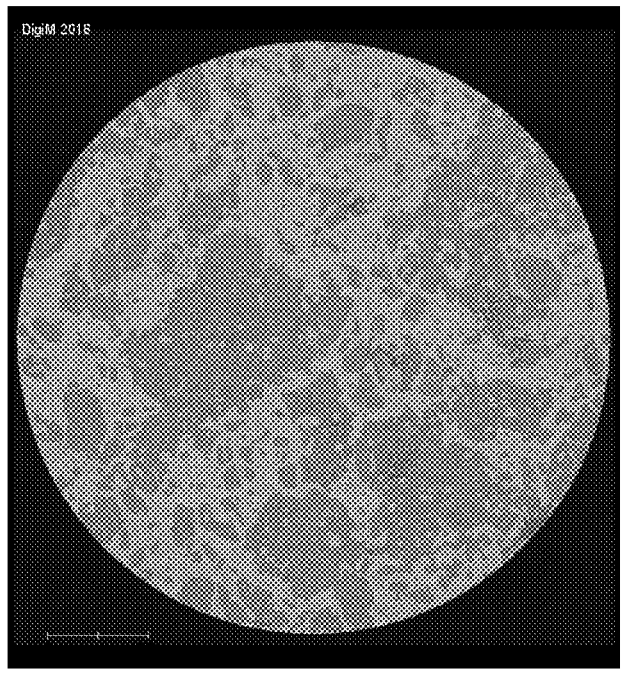
Figure 4D:
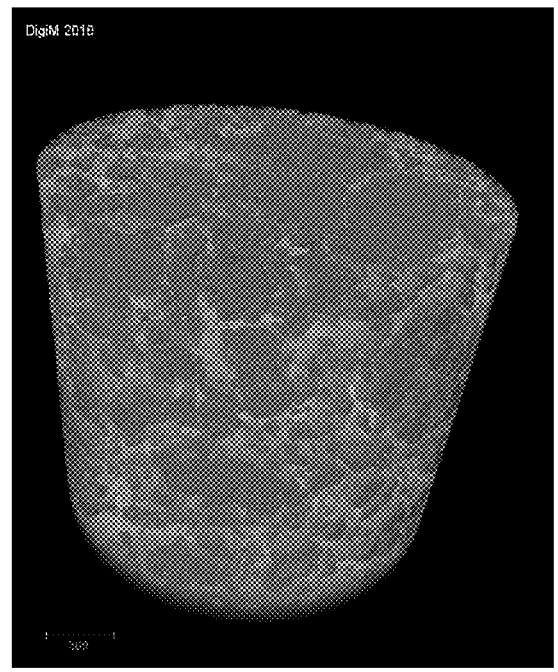

FIGS. 4A-4D show the phase segmentation (using block 222 of FIG. 2) results corresponding to the solid drug sample imaged in FIGS. 3A-3C. FIG. 4A shows one cross section of the XRM volume, with similar labeling to FIGS. 3A-3C. FIG. 4B shows the AI-based (block 242 of FIG. 2) segmentation on the three phases (annotated as 2 and 3 in FIG. 4A), using the same color scheme. The AI-segmentation is then applied to the full 3D data automatically (block 246 of FIG. 2, discussed in the next paragraph), shown as three cross sections in FIG. 4C, and full 3D volume visualization (block 241 of FIG. 2) in FIG. 4D.

Continuing with FIG. 2, the AI engine block (242) is further supported by high performance computing (HPC) block (246) and graphics processing unit (GPU) acceleration block (247), required to handle the computation of machine learning and deep learning algorithms in a massively parallel manner to ensure timely results.

Parameters used in the feature matrices will be exemplified in the discussion of the application of the method, herein.

Microstructure Equivalence Evaluation

Once the two feature matrices are obtained, microstructure equivalence evaluation follows.

To establish microstructure equivalence (Q3 BE), qualitative (Q1) and quantitative (Q2) BE needs to be first established (230). The parameters in the feature matrices are then compared quantitatively (231). With error tolerance evaluation (232) and necessary quality control (QC, 233), a Q3 BE report (234) can be generated. The report can be submitted to regulatory review. It can be archived in a regulatory Q3 BE database (235), which can be reused in the future.

If the Q3 BE evaluation reported that drug product A sample does not meet Q3 BE, the report along with the feature matrix data and their differences will provide important recommendations on process and formulation optimization (236) that can improve Q3 BE. Once the recommendation is implemented, drug product A samples with improved microstructure properties can go through block 200 to block 235 workflow iteratively, until Q3 BE reports affirmative BE evaluation.

FDA 21 CFR Part 11 Compliance and Good Data Practice

Systems, methods, and computer-readable media taught herein comply with FDA 21 CFR Part 11 requirements, and follow good data practice, block 244.

To ensure the validation of the computerized system, the system supports state of the art security (block 248) including strict user access rules, strong passwords, 2-step authentication, session and account expiration policies, and automatic user lockout after repeated failed login attempts.

An audit trail is created for all the image data, metadata, analysis operations, and user access history. The record cannot be modified. Audit trails can be reviewed, searched, and exported with digitalized certification. Version control and retention policy are supported.

An Embodiment Application Example of the Method

Figures 5A, 5B:
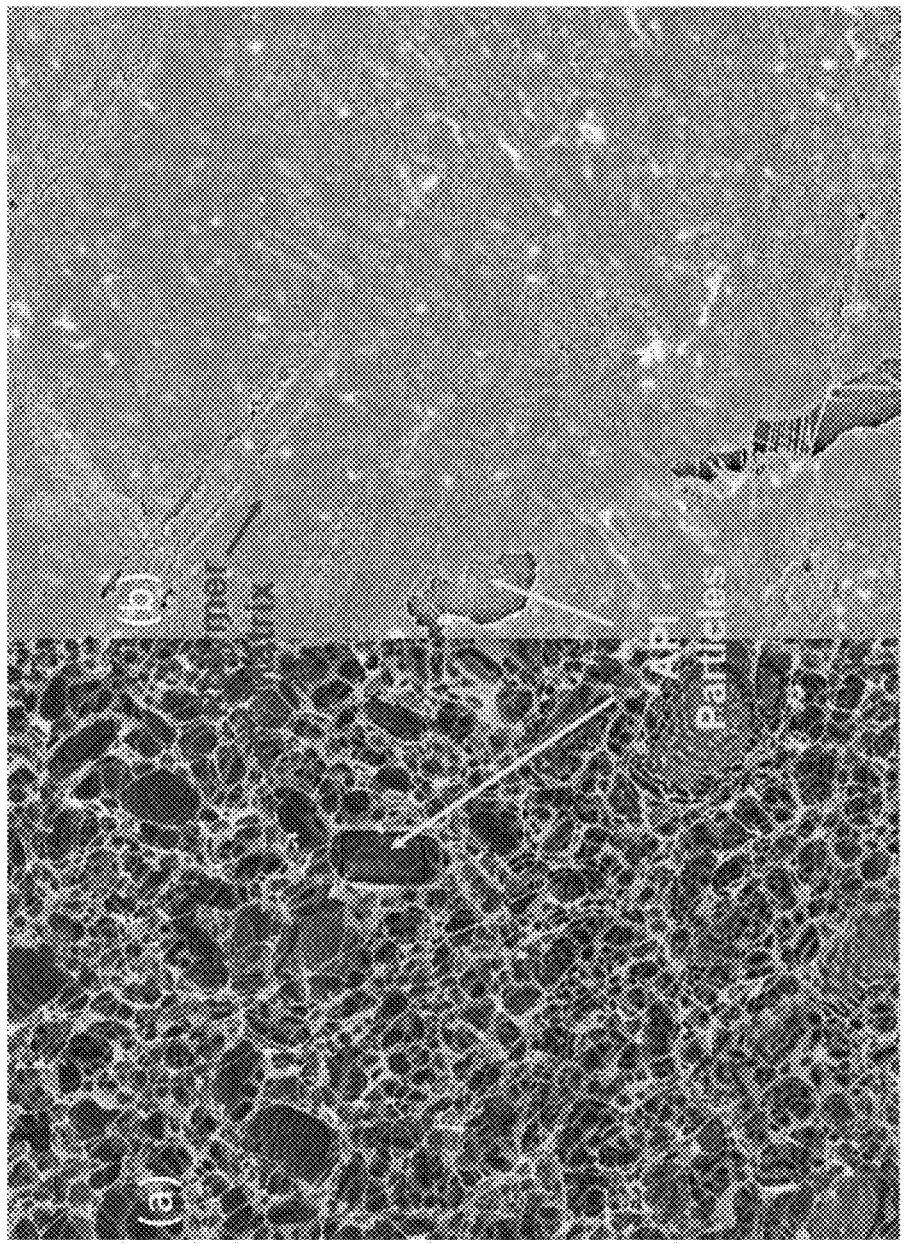
FIGS. 5A and 5B are example cross-sectional SEM images, which may be used to evaluate Q1 bioequivalence, in accordance with an embodiment of the invention.

Q1 and Q2 BEs may be necessary before Q3 BE. The system and method taught herein using microstructure imaging, AI-based image analytics, and image-based release modeling can provide support on Q1 and Q2 BE. FIGS. 5A and 5B show the microstructure imaging results of FENBID RLD (FIG. 5A; using block 2101 of FIG. 2) and a generic correspondence (FIG. 5B; using block 2102 of FIG. 2). Both drug samples were studied with focused ion beam scanning electron microscopy (block 200 of FIG. 2) at 50 nm resolution. It is clear that the RLD sample has API drug particles evenly distributed in a porous polymer matrix (blocks 202, 203, and 204 of FIG. 2), achieving an 8-hour constant controlled release rate (block 221 of FIG. 2). The generic drug sample has much less drug, much smaller pores, and salt precipitation alien (block 220 of FIG. 2) to the RLD sample. The microstructure imaging alone clearly show that they are not Q3 BE, nor Q1/Q2 BE. Further analysis is only needed if an improvement of the generic product to meet Q3 BE is desirable.

FIGS. 6A-6C show another example, an extended-release solid drug product, where Q1 of a generic drug sample has been established with its RLD. Using microstructure imaging and feature matrices, Q2 BE or the lack thereof can be established. FIG. 6A shows one cross-section of the XRM image of the RLD sample, where the API granule is quantified, in full 3D volume, as 52.8% of total drug volume, polymer matrix 46.2%, and porosity 1.6% (blocks 222, 223, 224, 221 of FIG. 2). A Q3 BE study using the system, method and computer-readable media taught herein was applied to the first lot of the generic drug products, FIG. 6B. A similar imaging and quantification shows 12.5% higher drug volume than the RLD sample, beyond the accepted tolerance of ±5% in weight (blocks 220, 230, 231, 232, 233, 234 of FIG. 2). Through a modification of processing conditions (block 236 of FIG. 2), samples from the optimized lot yields acceptable Q2 BE, as shown in FIG. 6C, which can be archived in the regulatory database for the reference of future generic abbreviated new drug application (ANDA) approval.

Q3 BE is a more stringent requirement on BE, as the particle and domain size, their distribution, and their interconnectivity needs to be evaluated as part of the microstructure feature matrix.

Figure 7A:
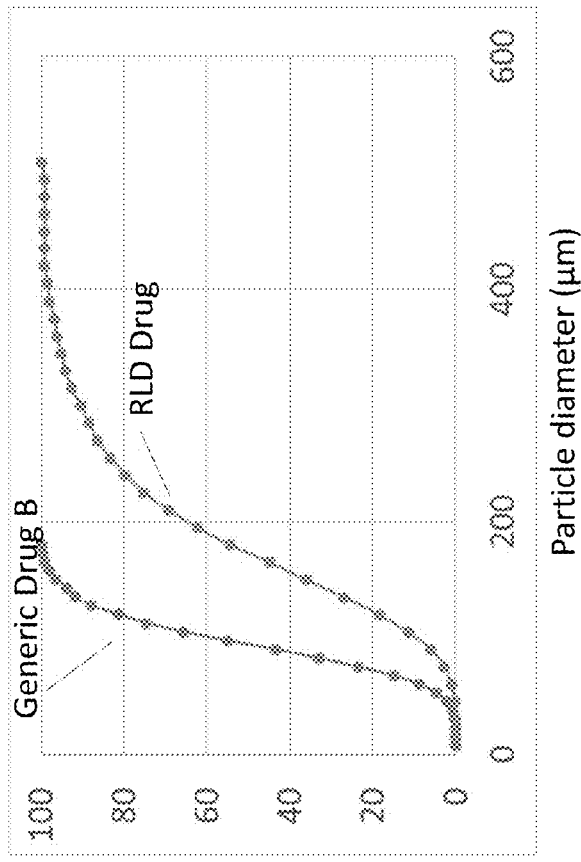
FIGS. 7A and 7B are graphs showing examples of particle size distributions (PSDs) used for a generic drug bioequivalence evaluation, in accordance with an embodiment of the invention.
Figure 7B:
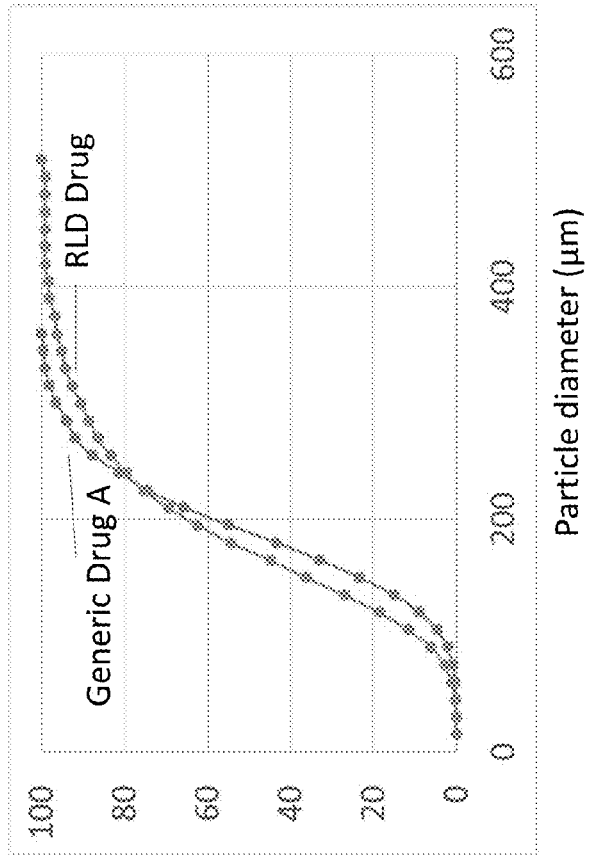

FIGS. 7A and 7B show the drug granule size distribution from two drug product samples, corresponding to API granule phase of the AI-segmented image volume shown in FIGS. 4A-4D. In this calculation, the segmented API granule phase is split with a watershed image processing algorithm, and a domain size distribution is calculated for each sample. FIG. 7A shows the comparison of the API particle size distribution (PSD) of Generic Drug Sample A and that of the RLD sample. The size distribution difference is within 5%, considered satisfactory to the size distribution required in Q3 BE. FIG. 7B shows another generic drug sample B, where the API size is substantially smaller than the RLD sample. More specifically, D10 is 30% smaller, D50 is 50% smaller, and D90 is 60% smaller. The failure of Q3 BE from image analysis, associated with much smaller API particle size, explains significantly faster release of Generic Drug B.

Figure 8B:
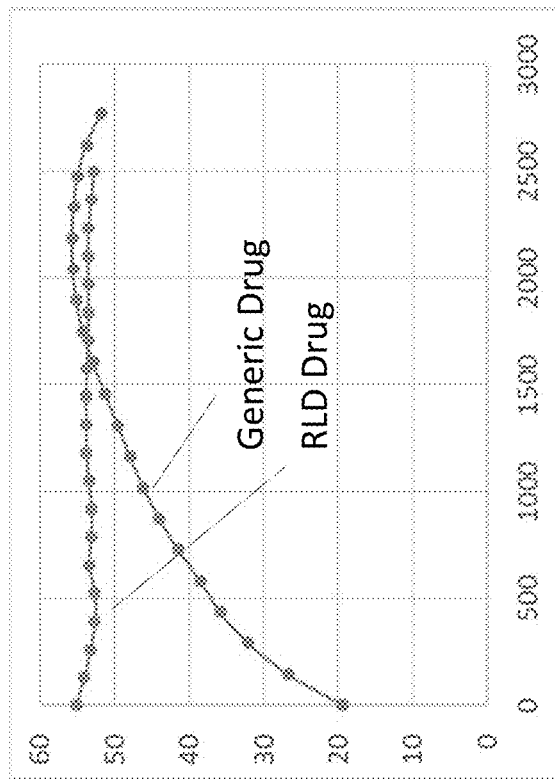
FIGS. 8A and 8B are examples of graphs showing spatial distribution uniformity evaluation, in accordance with an embodiment of the invention.
Figure 8A:
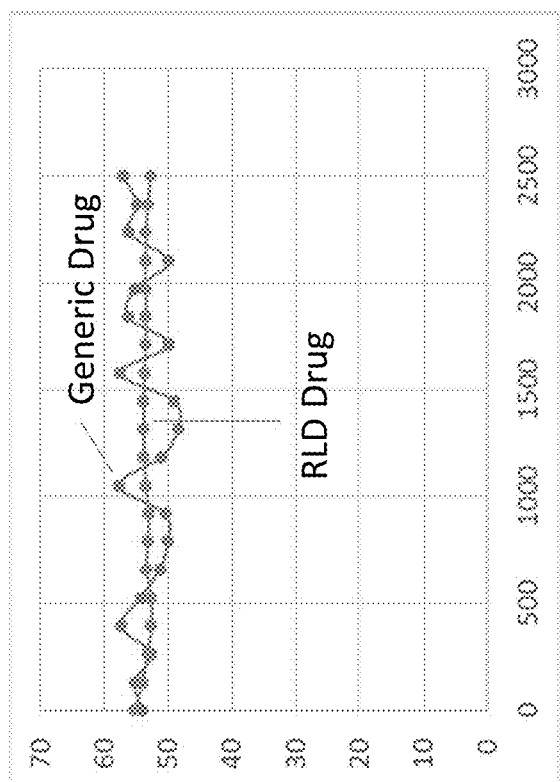

Domain size distribution equivalence is a necessary but insufficient condition for Q3 BE: the phase must also be spatially distributed in a comparable manner between the two drug products. FIG. 8A shows the spatial distribution of Generic Drug A in comparison with RLD Drug along the compaction direction of a tablet sample. Although the Generic Drug A sample does not have the supreme uniformity as the RLD sample, the variation is within ±5%. The uniformity is good enough for Q3 BE. In comparison, FIG. 8B shows the uniformity analysis of another Generic Drug B sample. The uniformity is significantly worse. At one location, the drug amount is only ⅓ of the expected drug amount, while the other location is higher than the desirable drug amount. Lack of uniformity poses a red flag for Q3 BE failure.

Figure 9A:
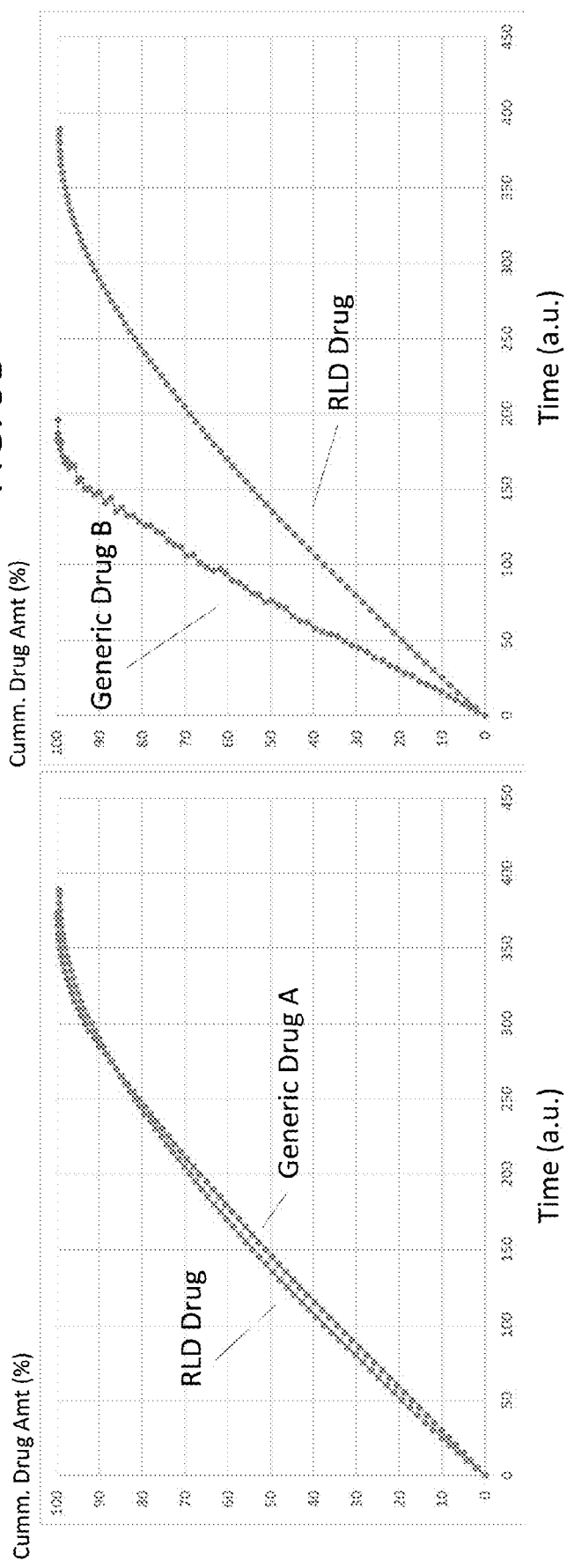
FIGS. 9A and 9B are examples of graphs of dissolution simulations, in accordance with an embodiment of the invention.
Figure 9B:
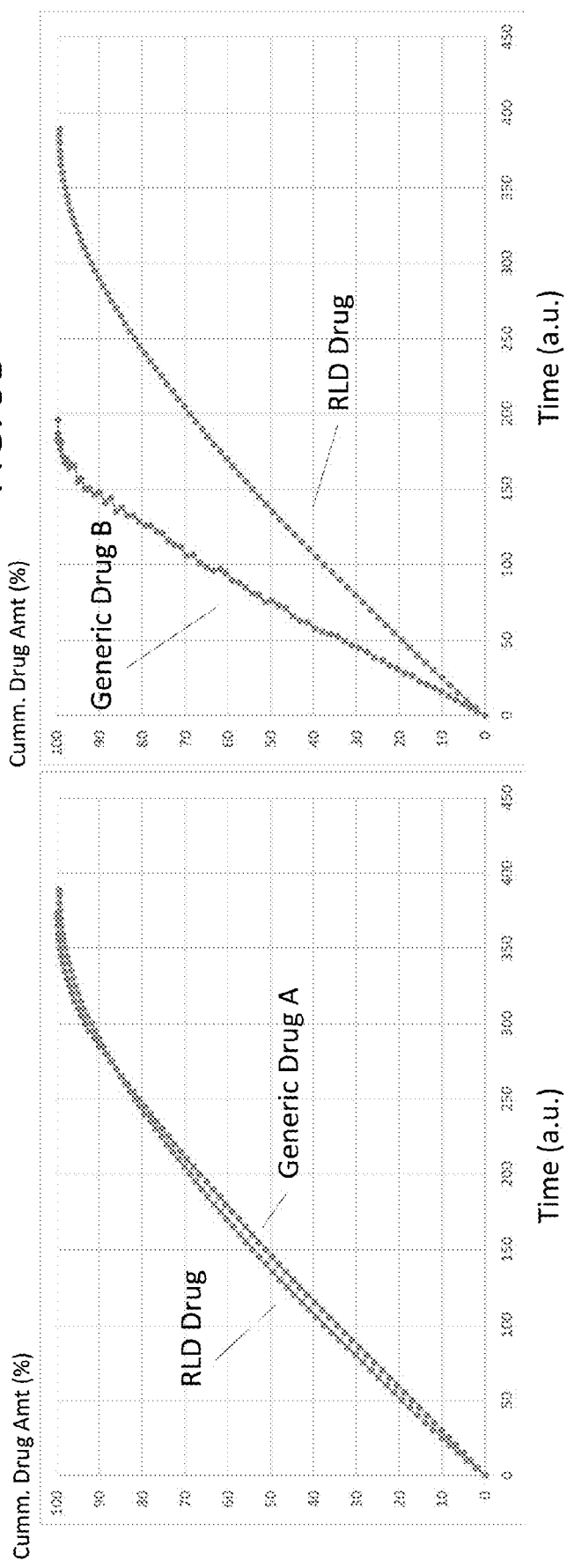

While domain size and uniformity are good indicators, they do not guarantee the equivalence of connectivity. Image-based transport modeling and release simulations can further solidify Q3 BE or lack thereof. FIGS. 9A and 9B show such examples. In FIG. 9A, release simulations were conducted on the 3D porous drug network reconstructed from 3D imaging data of Generic Drug A and RLD samples. The release curve compared favorably, with error less than 5%. In FIG. 9B, however, Generic Drug B sample has substantially faster release than RLD, suggesting Q3 BE failure even if the particle size and uniformity were proven to be equivalent.

An Embodiment of Equivalence Evaluation of Controlled Release Microspheres, Long-Acting Drug Products and Combination Products Microspheres have become an increasingly important delivery platform for the controlled release of a variety of drug products including small crystalline molecules, amorphous molecules, peptides, vaccine, and biologics. The encapsulation of active pharmaceutical ingredient (API) dispersed inside polymeric microspheres provides both flexibility in drug dosing and delivery route, and a superior engineering opportunity in achieving precise controlled release therapeutic performance. In vitro release testing methods, still predominant in product development, are costly due to the significant time and effort to develop and execute. Locally acting depots further render conventional PK/PD models, often developed, and validated for systemically circulating drug, ineffective. The size and complexity of polymeric microsphere formulations also challenge the effectiveness of conventional characterization methods in terms of resolution, turnaround time, and accuracy. With the supreme resolution improvement through 3D focused ion beam scanning electron microscopy (FIB-SEM) imaging, fast turnaround time with image-based release modeling, and proven accuracy with AI analytics, a 3D imaging and image-based release prediction method has been demonstrated on the ARESTIN® (minocycline HCl) microsphere product. As a promising alternative approach to understand the critical performance attributes, this new image-based method awaits further development and validation effort on additional products.

Despite the successful commercialization of several microsphere products, no generic microsphere products have been approved in the U.S. market yet. Difficulties arise from the challenge in establishing microstructure bioequivalence, due to a lack of fundamental understanding of the release mechanisms of these polymeric microsphere drug products, particularly for locally acting depot formulations. The transport-controlling microporous system often has pore throats as small as a few tens of nanometers to ensure long acting, sustained release over weeks to months. Complexity from the polymer-drug interplay, including polymer erosion, polymer swelling, and microporosity development obscures the boundary between trans-polymer diffusion transport and porous media transport. The uncertainties presented in generic development using conventional characterization methods are overwhelming. Despite the hindered development, investigations on the fundamental release mechanism of polymeric microspheres in direct association with microstructures remain largely absent. The need for a new, effective, and time and cost-efficient method is imminent.

For polymer-based microsphere products, microstructure of the API particles dispersed in a polymer matrix plays the most critical role in product performance. In establishing the equivalence of two drug products, the API particle sizes in the final drug product, the uniformity of API inter- and intra-microsphere distributions, and matching release profile are among the critical performance attributes (CPA). In-vitro and in-vivo tests are costly, yet incapable of decoding the drug-polymer-porosity interplay. Formulation and process development are hence largely a practice of trial and error, which challenges new drug development budget and intimidates generic development despite high potential market impact and interest.

Recognizing the importance of resolution and the need of assessing the internal structure of microsphere products, mechanical cutting and 2D imaging using Scanning Electron Microscopy (SEM), light microscopy, and Raman microscopy have been used. However, these 2D methods have limitations due to mechanical cutting artefacts and difficulty. Therapeutic performance evaluation associated with API transport requires assessment on the interconnected network of API, polymer, and porosity, which cannot be achieved in 2D.

FIB-SEM is a new generation electron microscopy imaging platform that supports 3D imaging with nanometer resolution. Gallium ion FIB can mill a thin layer of material away from the sample and expose sample cross section for high resolution field emission SEM imaging. Iterative FIB milling and SEM imaging produces a stack of SEM images at 3 nm-50 nm resolution that can be reconstructed into a 3D digital representation of a microsphere sample. FIB-SEM has been demonstrated to successfully characterize PLGA based ARESTIN® sustained release microsphere product containing minocycline HCl. Comparing to mechanical cutting commonly used in microsphere subsurface microstructure characterization, FIB-SEM can visualize an artifact-free cross section surface with microstructure detail accurately maintained and presented. Energy dispersion X-Ray spectroscopy (EDS) detector can be used, in combination with FIB-SEM, to collected X-Ray signal and characterize chemical composition on FIB-SEM cross section surfaces. The digitized microsphere sample in 3D via FIB-SEM imaging experiment can then be analyzed with an artificial intelligence (AI)-based image analysis engine, to quantify the size and uniformity of the API phase. Release profiles and physical properties can be predicted by combining the microstructure models reconstructed from the images with computational physics engine solving transport equations directed on the imaged microstructure voxels.

While FIB-SEM provided non-precedented 3D resolution, it can only study one microsphere at a time. Sample representativeness hence requires additional considerations. In this project, a correlative imaging technique will be used. X-Ray Microscopy (XRM) will be employed to image non-invasively tens of milligram of samples, including thousands of microspheres. The 3D tomographic data can assist in evaluations of inter-microsphere homogeneity, detections of recrystallization, impurity, and void, and determine the target microsphere specimen for FIB-SEM. The collected multi-resolution data can then be integrated using a multi-scale representative elementary volume (REV) model, where release profile can be predicted. The multi-scale REV model was developed and verified on material samples outside pharmaceutical industry.

Since generic companies have little or no knowledge of the processing methods used in the manufacture of the RLD product, it is critically important to develop a comprehensive understanding of the relationship between KPA and product performance as well as an associated suite of repeatable, validated, and quality controlled methods whereby microstructure properties can be rapidly assessed and correlated with in vitro and in vivo product performance. Using an embodiment of this invention, CPAs of polymeric microsphere products in support of ANDA approval of complex, long-acting polymeric microsphere drug products. A combination of correlative imaging digital transformation modules, microstructure AI quantification modules, and therapeutic performance evaluation modules through image-based release prediction modules to establish a matrix of CPAs. A feedback-loop workflow is demonstrated where the imaging KPA can advance mechanistic understandings on the therapeutic performance at microstructure level and guide the optimization of formulation and manufacturing process to achieve desirable performance. Validation protocol, reusable regulatory database, good data practice protocol with FDA 21 CFR Part 11 compliance, and AI platform technology further provides critical supporting technologies. A reusable microsphere digital database with imaging data, CPA, and performance evaluation history of both RLD and approved generics, with full audit trail, that can better support complex polymer-based microsphere generic drug products development and regulatory approval.

An example feedback workflow is here provided to support a generic microsphere drug performance evaluation, specifically in establishing microstructure equivalence with CPAs between a generic microsphere sample and a RLD sample. Starting from two microsphere samples, one generic, one RLD, correlative imaging (FIG. 2, blocks 200 and 210) ensures 3D imaging of the samples in a consistent, representative manner. The 3D imaging data from both samples will go through a collection of digital transformations (blocks 222, 223 and 224 of FIG. 2) including AI image segmentation, feature extraction, and phase quantification. Using blocks 220 and 221, the segmented images will then be statistically analysed to get CPAs such as API particle size distribution and API uniformity. Image-based release simulations further predicts additional CPAs such as release profiles. The resulting CPAs from the two samples will be compared quantitatively (blocks 231). If a CPA equivalence is not achieved, recommendations will be used as feedback to the optimization module (blocks 236) for further optimization. The improved samples will be tested in vitro, while another iteration of image-based CPA evaluation is conducted. More than one iteration might be necessary, though the number of iterations is expected to be significantly smaller than the conventional formulation and process optimization approach.

The workflow is in fully compliance with FDA 21 CFR Part 11 compliance (module D). All processing steps and parameters are traceable for both repeatability and auditing purposes.

Figure 10:
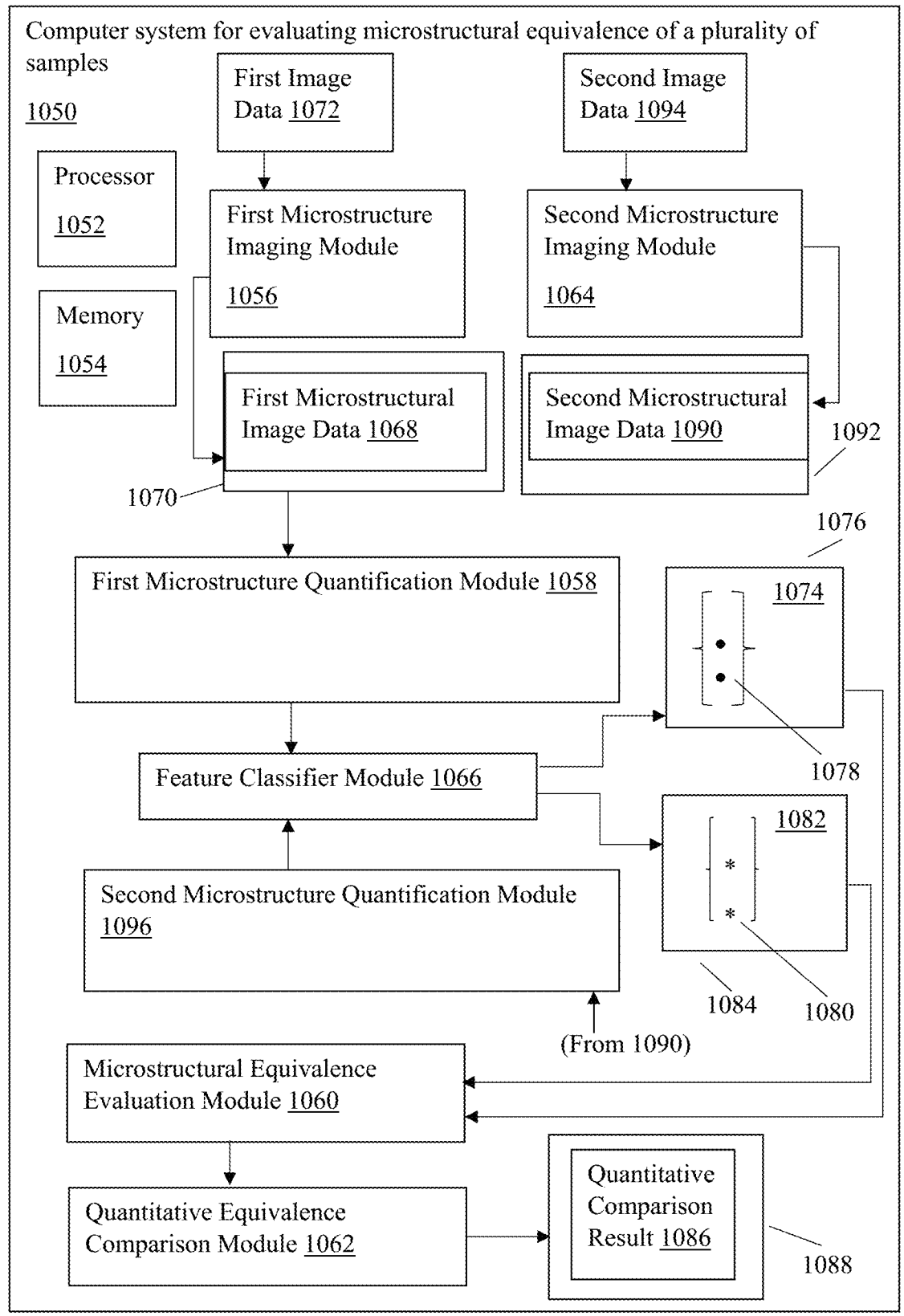
FIG. 10 is a schematic block diagram of a computer system for evaluating microstructural equivalence of a plurality of samples, in accordance with an embodiment of the invention.

Further Schematic Discussion of the Systems, Methods, and Computer-Readable Media FIG. 10 is a schematic block diagram of a computer system 1050 for evaluating microstructural equivalence of a plurality of samples, in accordance with an embodiment of the invention. In FIG. 10, the computer system 1050 includes a processor 1052 and a memory 1054, which stores computer code instructions. The processor 1052 and the memory 1054, with the computer code instructions, are configured to implement: a first microstructure imaging module 1056, first microstructure quantification module 1058, a microstructural equivalence evaluation module 1060, and quantitative equivalence comparison module 1062. The processor 1052 and memory 1054 may also be configured to implement second microstructure imaging module 1064 and feature classifier module 1066. In addition, the processor 1052 and memory 1054 may be configured to implement and make use of other modules and data structures taught herein, such as modules and data structures in FIGS. 1, 2, and 10. It will be appreciated that processor 1052 and memory 1054 may be implemented on one or more separate processors and one or more separate memories, any combination of which cooperate to implement all or a portion of embodiments herein.

In the embodiment of FIG. 10, the computer system 1050 comprises a first microstructure imaging module 1056 configured to generate first microstructural image data 1068, stored in a first image data structure 1070, in a manner automated by processor 1052, based on first image data 1072 of a microstructure of a first sample. A first microstructure quantification module 1058 is configured to quantify the microstructure of the first sample, in a manner automated by the processor 1052. The quantifying comprises generating a first microstructure feature matrix 1074 of the first microstructure based on the first microstructural image data 1068, where the first microstructure feature matrix 1074 is stored in a first feature matrix data structure 1076. A microstructural equivalence evaluation module 1060 is configured to evaluate microstructural equivalence of the first sample with a second sample, in a manner automated by the processor 1052, by quantitatively comparing parameters 1078 of the first microstructure feature matrix 1074 with corresponding parameters 1080 of a second microstructure feature matrix 1082 for the second sample, with the second microstructure feature matrix 1082 being stored in a second feature matrix data structure 1084. A quantitative equivalence comparison module 1062 is configured to provide, in a manner automated by the processor 1052, a quantitative comparison result 1086 stored in a comparison result data structure 1088, to permit evaluating whether the plurality of samples meet a microstructural equivalence standard within an error tolerance based on results of the quantitatively comparing of the corresponding parameters of the first microstructure feature matrix 1074 and the second microstructure feature matrix 1082. For example, the evaluating error tolerance by module 1062 (see also 232 of FIG. 2) can include using processor 1052 to determine whether or not each of the corresponding parameters of the microstructure feature matrices 1074 and 1082 are within a quantified error tolerance, stored in a data structure such as database 243 (see FIG. 2), that is permitted for each set of corresponding parameters, such as determining whether each of the parameters of the first feature matrix are within one or more of within plus or minus 20%, plus or minus 10%, or plus or minus 5%, of the corresponding parameter of the second feature matrix. It will be appreciated that different error tolerances for each of the corresponding parameters may be used. The quantitative comparison result 1086 can be in a variety of different possible forms of quantified results, stored in a data structure such as database 243 (see FIG. 2), such as: a binary data indication or indications that one or more of the parameters of the microstructure feature matrices 1074 and 1082 are, or are not, within the quantified error tolerance of each other; or one or more values indicating the difference between such parameters; or one or more values indicating a number of standard deviations or percentages by which the parameters differ from each other; or another form of comparison result for the parameters, stored in a data structure such as database 243, in a manner automated by processor 1052.

The computer system 1050 of FIG. 10 may further comprise a second microstructure imaging module 1064 configured to generate second microstructural image data 1090, stored in a second image data structure 1092, in a manner automated by the processor 1052, based on second image data 1094 of a microstructure of the second sample. This can, for example, be done when the second sample has not yet been characterized. In other embodiments, the second sample may already have been characterized, in which case the second microstructure imaging module 1064 may not be needed. If it is used, a second microstructure quantification module 1096 may be configured to quantify the microstructure of the second sample, in a manner automated by the processor 1052, the quantifying comprising generating the second microstructure feature matrix 1082 of the second microstructure based on the second microstructural image data 1090. The system may be configured to evaluate bioequivalence of a plurality of pharmaceutical products, in a manner automated by the processor 1052, to evaluate whether the plurality of pharmaceutical products comprise a same component, in a same concentration, in a same microstructural arrangement of matter, within an error tolerance— for example, to meet a Q3 Bioequivalence standard. Here, determining whether bioequivalence is within the error tolerance can be evaluated by the processor 1052 in similar fashion to that described above discussion of error tolerance. The first sample may comprise a first drug product, and the second sample may comprise a sample of a reference drug product, and the microstructural equivalence evaluation module 1060 may be configured to evaluate equivalence of the plurality of microstructures at least by, in a manner automated by the processor 1052, evaluating bioequivalence of the first drug product with the reference drug product. For example, the first sample can comprise a sample of a product seeking regulatory approval, such as a generic product, a product subjected to scale up and post-approval changes, or a new product in clinical trial that is subjected to a slight change in formulation, ingredients, component manufactures, and process; and the second sample can, for example, comprise a reference listed brand product or a product before change. The first microstructure feature matrix 1074, stored in the first feature matrix data structure 1076, and the second microstructure feature matrix 1082, stored in the second feature matrix data structure 1084, may comprise corresponding matrix parameters 1078, 1080 for at least one of: particle size distribution of a material phase, porosity of the material phase, uniformity of spatial distribution of the material phase, and release rate of the material phase. The technique can include comparing a selection of such parameters, and can include comparing all of the foregoing parameters, to evaluate microstructural equivalence. The computer system 1050 may comprise a feature classifier module 1066 configured to generate the first microstructure feature matrix 1074, stored in the first feature matrix data structure 1076, in a manner automated by the processor 1052 by producing the corresponding matrix parameters of the first microstructure feature matrix 1074. Likewise, the feature classifier module 1066 may be configured to generate the second microstructure feature matrix 1082, stored in the second feature matrix data structure 1084, in a manner automated by the processor 1052 by producing the corresponding matrix parameters of the second microstructure feature matrix 1082. At least one of the first microstructural image data 1068 stored in the first image data structure 1070 and the second microstructural image data 1090 stored in the second image data structure 1092 comprises phase segmented image data based at least in part on use of an artificial intelligence engine (see 242 in FIG. 2) to produce the phase segmented image data. The system may be configured to compute the release rate of the material phase with an image-based release prediction model in a manner automated by the processor 1052. Each of the first image data 1068 and the second image data 1094 may comprise at least one of: x-ray microscopy (XRM) imaging data and focused ion beam scanning electron microscopy (FIB-SEM) imaging data; and may comprise grayscale voxel value data.

Figure 11:
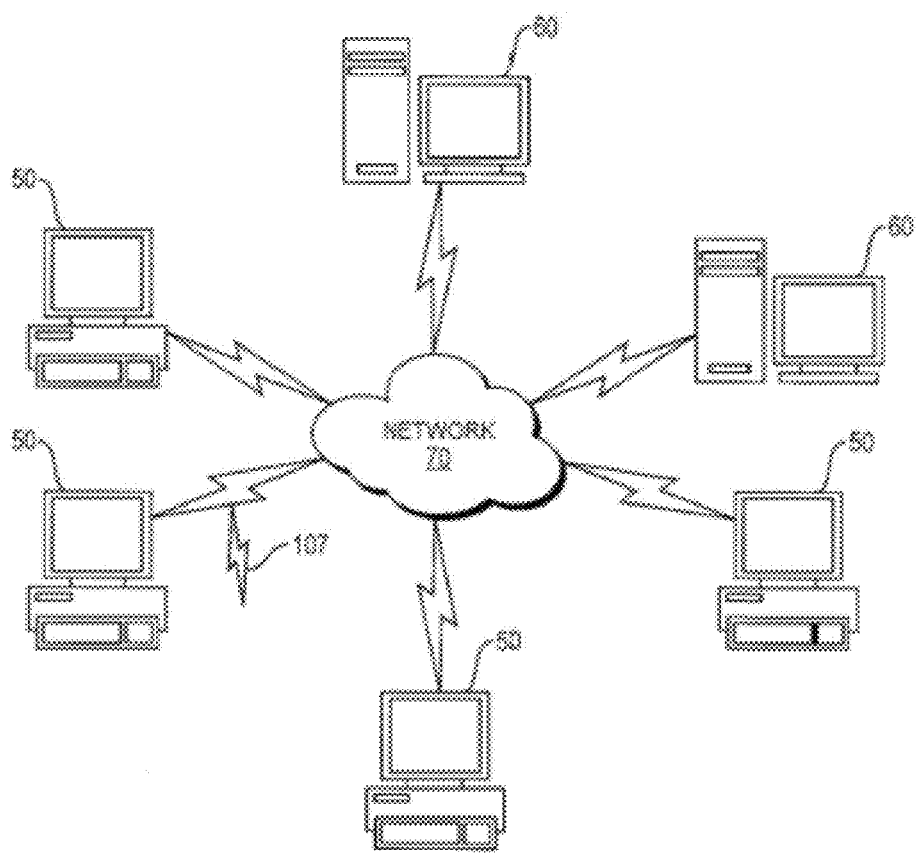
FIG. 11 illustrates a computer network or similar digital processing environment in which embodiments of the present invention may be implemented.

FIG. 11 illustrates a computer network or similar digital processing environment in which embodiments of the present invention may be implemented. Client computer(s)/devices 50 and server computer(s) 60 provide processing, storage, and input/output devices executing application programs and the like. The client computer(s)/devices 50 can also be linked through communications network 70 to other computing devices, including other client devices/processes 50 and server computer(s) 60. The communications network 70 can be part of a remote access network, a global network (e.g., the Internet), a worldwide collection of computers, local area or wide area networks, and gateways that currently use respective protocols (TCP/IP, Bluetooth®, etc.) to communicate with one another. Other electronic device/computer network architectures are suitable.

Figure 12:
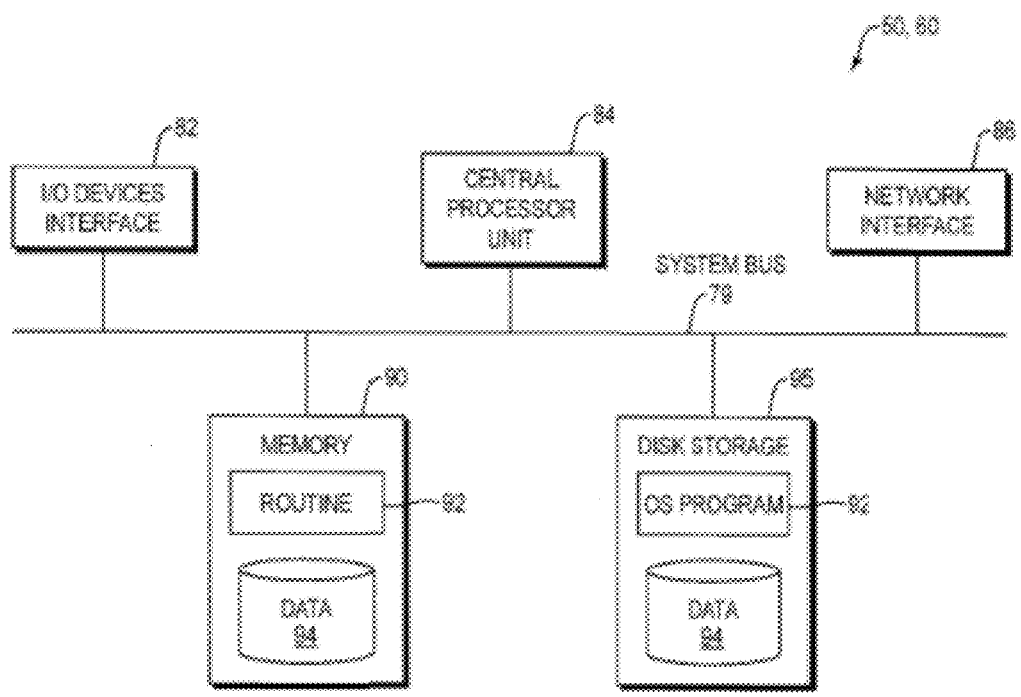
FIG. 12 is a diagram of an example internal structure of a computer in the computer system of FIG. 11.

FIG. 12 is a diagram of an example internal structure of a computer (e.g., client processor/device 50 or server computers 60) in the computer system of FIG. 11. Each computer 50, 60 contains a system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) that enables the transfer of information between the elements. Attached to the system bus 79 is an I/O device interface 82 for connecting various input and output devices (e.g., keyboard, mouse, displays, printers, speakers, etc.) to the computer 50, 60. A network interface 86 allows the computer to connect to various other devices attached to a network (e.g., network 70 of FIG. 11). Memory 90 provides volatile storage for computer software instructions 92 and data 94 used to implement an embodiment of the present invention (including, for example, to implement one or more of: the modules of FIGS. 1, 2, and 10, and their methods, and corresponding data structures, detailed herein). Disk storage 95 provides non-volatile storage for computer software instructions 92 and data 94 used to implement an embodiment of the present invention. A central processor unit 84 is also attached to the system bus 79 and provides for the execution of computer instructions, for example having a flow of data and control as taught herein.

In one embodiment, the processor routines 92 and data 94 are a computer program product (generally referenced 92), including a non-transitory computer-readable medium (e.g., a removable storage medium such as one or more DVD-ROM's, CD-ROM's, diskettes, tapes, etc.) that provides at least a portion of the software instructions for the invention system. The computer program product 92 can be installed by any suitable software installation procedure, as is well known in the art. In another embodiment, at least a portion of the software instructions may also be downloaded over a cable communication and/or wireless connection 107. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals may be employed to provide at least a portion of the software instructions for the present invention routines/program 92.

In alternative embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer.

In other embodiments, the software instructions 92 and data 94 are provided on a cloud platform, as SaaS (Software as a Service), and the like.

REFERENCES

1. The Pharmaceutical Development Group: The Importance of Generic Drugs. https://pharmadevgroup.com/importance-and-excellent-benefits-of-generic-drugs/
2. Drugs@FDAGlossaryofTerms https://www.fda.gov/drugs/drug-approvals-and-databases/drugsfda-glossary-terms#RLD
3. AAPS Advances in the Pharmaceutical Sciences Series 13: FDA Bioequivalence standards. Eds. Lawrence X. Yu, Bing V. Li. Springer 2014. https://doi.org/1007/978-1-4939-1252-0
4. Gajjar, P et al. Respiratory Drug Delivery 2020) https://ubra.herts.ac.uk/bitstream/handle/2299/22724/GajjarEtAl_RDD2020_2020.pdf?sequence=1&isAllowed=y
5. Kryscio D R et al. AAPS PharmSciTech 2008, 9: 84-6 https://www.ncbi.nlm.nih.gob/pmc/articles/PMC2976873/
6. FDA Bioequivalence Pathways https:www.fda.gov/media/91553/download
7. Zhao L et. al. J Biomed Biotechnol. 2012; 2012:507294. doi: 10.1155/2012/507294. Epub 2012 July 15. https://pubmed.ncbi.nlm.nih.gov/22911056
8. The University of Cambridge—Raman Spectroscopy http://web.archive.org/web/20120511102714/http://www.doitpoms.ac.uk/tlplib/raman/intro.php
9. Mayo S C et al., Materials 2012, 5: 937-65 https://www.mdpi.com/1996-1944/5/5/937
10. Chen G-H, et al. Curr Med Imaging Rev 2010, 6: 90-9. https://www.ncbi.nlm.nih.gov/pmc/articles/PMC3747977/

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A computer-implemented method of evaluating microstructural equivalence of a plurality of samples, the computer-implemented method comprising:
    generating first microstructural image data, stored in a first image data structure, in a manner automated by a processor, based on first image data of a microstructure of a first sample;
    quantifying the microstructure of the first sample, in a manner automated by the processor, the quantifying comprising generating a first microstructure feature matrix of the first microstructure based on the first microstructural image data, the first microstructure feature matrix stored in a first feature matrix data structure; and
    evaluating microstructural equivalence of the first sample with a second sample, in a manner automated by the processor, by quantitatively comparing parameters of the first microstructure feature matrix with corresponding parameters of a second microstructure feature matrix for the second sample, the second microstructure feature matrix stored in a second feature matrix data structure; and
    providing, in a manner automated by the processor, a quantitative comparison result stored in a comparison result data structure, to permit evaluating whether the plurality of samples meet a microstructural equivalence standard within an error tolerance based on results of the quantitatively comparing of the corresponding parameters of the first microstructure feature matrix and the second microstructure feature matrix.

2. The computer-implemented method of claim 1, further comprising:
    generating second microstructural image data, stored in a second image data structure, in a manner automated by the processor, based on second image data of a microstructure of the second sample; and
    quantifying the microstructure of the second sample, in a manner automated by the processor, the quantifying comprising generating the second microstructure feature matrix of the second microstructure based on the second microstructural image data.

3. The computer-implemented method of claim 2, wherein the second image data comprises at least one of: x-ray microscopy (XRM) imaging data and focused ion beam scanning electron microscopy (FIB-SEM) imaging data with appropriate contrast and calibration mechanisms.

4. The computer-implemented method of claim 1, wherein the evaluating equivalence of the plurality of microstructures comprises evaluating bioequivalence of a plurality of pharmaceutical products, in a manner automated by the processor, to evaluate whether the plurality of pharmaceutical products comprise a same component, in a same concentration, in a same microstructural arrangement of matter, within an error tolerance.

5. The computer-implemented method of claim 1, wherein the first sample comprises a first drug product, and wherein the second sample comprises a sample of a reference drug product, and wherein the evaluating equivalence of the plurality of microstructures comprises, in a manner automated by the processor, evaluating bioequivalence of the first drug product with the reference drug product.

6. The computer-implemented method of claim 5, wherein the first drug product comprises a generic drug product, the method comprising performing more than one iteration of:
   performing correlative imaging of the first drug product and the reference drug product to produce three-dimensional imaging data of the first drug product and the reference drug product;
   performing image segmentation of the three-dimensional imaging data of the first drug product and the reference drug product to product segmented three-dimensional imaging data;
   statistically analyzing the segmented three-dimensional imaging data to produce critical performance attributes of the first drug product and the reference drug product;
   performing image-based release simulations to obtain at least one additional critical performance attribute of the first drug product and the reference drug product;
   quantitatively comparing the critical performance attributes of the first drug product and the reference drug product to evaluate the bioequivalence of the first drug product with the reference drug product;
   if bioequivalence is not found in the comparing of the critical performance attributes, generating optimization feedback for a further iteration of image-based bioequivalence evaluation.

7. The computer-implemented method of claim 6, wherein each of the first drug product and the reference drug product comprises a drug product from the group consisting of: a long-acting polymeric microsphere, an implant, a device, a complex drug, and a combination drug.

8. The computer-implemented method of claim 1, wherein the first microstructure feature matrix, stored in the first feature matrix data structure, and the second microstructure feature matrix, stored in the second feature matrix data structure, comprise corresponding matrix parameters for at least one of: particle size distribution of a material phase, porosity of the material phase, uniformity of spatial distribution of the material phase, dissolution rate of the material phase, and release rate of the material phase.

9. The computer-implemented method of claim 8, wherein generating the first microstructure feature matrix, stored in the first feature matrix data structure, comprises using a feature classifier module in a manner automated by the processor to produce the corresponding matrix parameters of the first microstructure feature matrix.

10. The computer-implemented method of claim 9, wherein generating the second microstructure feature matrix, stored in the second feature matrix data structure, comprises using a feature classifier module in a manner automated by the processor to produce the corresponding matrix parameters of the second microstructure feature matrix.

11. The computer-implemented method of claim 8, wherein at least one of the first microstructural image data stored in the first image data structure and the second microstructural image data stored in the second image data structure comprises phase segmented image data based at least in part on use of an artificial intelligence engine to produce the phase segmented image data.

12. The computer-implemented method of claim 8, wherein the release rate of the material phase is computed with an image-based release prediction model in a manner automated by the processor.

13. The computer-implemented method of claim 1, wherein the first image data comprises at least one of: x-ray microscopy (XRM) imaging data and focused ion beam scanning electron microscopy (FIB-SEM) imaging data with appropriate contrast and calibration mechanisms.

14. A computer system for evaluating microstructural equivalence of a plurality of samples, the computer system comprising:
   a first microstructure imaging module configured to generate first microstructural image data, stored in a first image data structure, in a manner automated by a processor, based on first image data of a microstructure of a first sample;
   a first microstructure quantification module configured to quantify the microstructure of the first sample, in a manner automated by the processor, the quantifying comprising generating a first microstructure feature matrix of the first microstructure based on the first microstructural image data, the first microstructure feature matrix stored in a first feature matrix data structure;
   a microstructural equivalence evaluation module configured to evaluate microstructural equivalence of the first sample with a second sample, in a manner automated by the processor, by quantitatively comparing parameters of the first microstructure feature matrix with corresponding parameters of a second microstructure feature matrix for the second sample, the second microstructure feature matrix stored in a second feature matrix data structure; and
   a quantitative equivalence comparison module configured to provide, in a manner automated by the processor, a quantitative comparison result stored in a comparison result data structure, to permit evaluating whether the plurality of samples meet a microstructural equivalence standard within an error tolerance based on results of the quantitatively comparing of the corresponding parameters of the first microstructure feature matrix and the second microstructure feature matrix.

15. The computer system of claim 14, wherein the first sample comprises a first drug product, and wherein the second sample comprises a sample of a reference drug product, and wherein the microstructural equivalence evaluation module is configured to evaluate equivalence of the plurality of microstructures at least by, in a manner automated by the processor, evaluating bioequivalence of the first drug product with the reference drug product.

16. The computer system of claim 14, wherein the first microstructure feature matrix, stored in the first feature matrix data structure, and the second microstructure feature matrix, stored in the second feature matrix data structure, comprise corresponding matrix parameters for at least one of: particle size distribution of a material phase, porosity of the material phase, uniformity of spatial distribution of the material phase, and release rate of the material phase.

17. The computer system of claim 16, comprising a feature classifier module configured to generate at least one of: (i) the first microstructure feature matrix, stored in the first feature matrix data structure, in a manner automated by the processor by producing the corresponding matrix parameters of the first microstructure feature matrix, and (ii) the second microstructure feature matrix, stored in the second feature matrix data structure, in a manner automated by the processor by producing the corresponding matrix parameters of the second microstructure feature matrix.

18. The computer system of claim 16, wherein at least one of the first microstructural image data stored in the first image data structure and the second microstructural image data stored in the second image data structure comprises phase segmented image data based at least in part on use of an artificial intelligence engine to produce the phase segmented image data.

19. The computer system of claim 16, wherein the system is configured to compute the release rate of the material phase with an image-based release prediction model in a manner automated by the processor.

20. A non-transitory computer-readable medium configured to store instructions for evaluating microstructural equivalence of a plurality of samples, the instructions, when loaded into working memory and executed by a processor, cause the processor to evaluate microstructural equivalence of the plurality of samples by:

generating first microstructural image data, stored in a first image data structure, in a manner automated by a processor, based on first image data of a microstructure of a first sample;

quantifying the microstructure of the first sample, in a manner automated by the processor, the quantifying comprising generating a first microstructure feature matrix of the first microstructure based on the first microstructural image data, the first microstructure feature matrix stored in a first feature matrix data structure; and evaluating microstructural equivalence of the first sample with a second sample, in a manner automated by the processor, by quantitatively comparing parameters of the first microstructure feature matrix with corresponding parameters of a second microstructure feature matrix for the second sample, the second microstructure feature matrix stored in a second feature matrix data structure; and providing, in a manner automated by the processor, a quantitative comparison result stored in a comparison result data structure, to permit evaluating whether the plurality of samples meet a microstructural equivalence standard within an error tolerance based on results of the quantitatively comparing of the corresponding parameters of the first microstructure feature matrix and the second microstructure feature matrix.

* * * * *